United States Patent [19]

Hennart et al.

[11] 4,058,607

[45] Nov. 15, 1977

[54] INSECTICIDE EVAPORATOR COMPRISING A STABILIZER

[75] Inventors: Claude Hennart, Aubervilliers; Marcel Louis Dulat, Poitiers, both of France

[73] Assignee: Airwick Industries, Inc., Carlstadt, N.J.

[21] Appl. No.: 671,982

[22] Filed: Mar. 30, 1976

Related U.S. Application Data

[63] Continuation-in-part of Ser. No. 380,129, July 17, 1973, Pat. No. 3,962,415, which is a continuation-in-part of Ser. No. 180,507, Sept. 14, 1971, Pat. No. 3,852,439.

[51] Int. Cl.² ........................... A01N 9/36; A01N 9/28; A01N 9/20
[52] U.S. Cl. .................................... 424/219; 424/226; 424/278; 424/282; 424/327
[58] Field of Search ................... 424/19, 33, 175, 219, 424/226, 282, 327, 278

[56]  References Cited

U.S. PATENT DOCUMENTS

| 3,155,568 | 11/1964 | Surgant et al. | 424/175 |
|---|---|---|---|
| 3,338,783 | 8/1967 | Popjak | 424/219 |
| 3,620,453 | 11/1971 | Gancberg et al. | 424/219 |
| 3,705,941 | 12/1972 | Hennart et al. | 424/219 |

*Primary Examiner*—V. D. Turner
*Attorney, Agent, or Firm*—Wenderoth, Lind & Ponack

[57]  ABSTRACT

Insecticide evaporator comprising at least one volatile phosphoric ester insecticide, an agent for stabilizing the said ester against decomposition by protonization and used in an amount of 0.2 to 20% based on the weight of phosphoric ester, characterized in that the stabilizing agent contains at least one compound selected from the compounds of the chemical class of 1,3-benzodioxoles and at least one diazene.

9 Claims, No Drawings

INSECTICIDE EVAPORATOR COMPRISING A STABILIZER

RELATIONSHIP TO EARLIER APPLICATION

This application is a continuation-in-part patent application of our pending patent application Ser. No. 380,129 filed on July 17, 1973 now U.S. Pat. No. 3,962,415, which in turn is a continuation-in-part patent application of patent application Ser. No. 180,507 now U.S. Pat. No. 3,852,439 filed on Sept. 14, 1971.

BACKGROUND OF THE INVENTION

Volatile phosphoric esters are now widely used as pesticides, particularly as evaporator insecticides. Their wide use is due principally to their rapid action as vapors and the absence of any accumulation of the compounds in living tissue as a result of their rapid hydrolysis in situ.

This last characteristic, which gives a net advantage over "chlorinated" pesticides, is on the other hand, a serious disadvantage: the sensitivity of certain phosphoric acid esters to humidity, even just that of the atmosphere, is such that decomposition takes place in the evaporator before evaporation and before they are able to act on the pest organisms. The esters particularly susceptible to this are those containing low alkyl groups such as methyl, ethyl, propyl or isopropyl attached to the phosphoric anion. On contact with molecules of water, at least partial decomposition of the esters takes place by protonisation, i.e. by replacement of a low alkyl group by hydrogen.

Among the sensitive phosphoric esters, special mention should be made of 0-2,2-dichlorovinyl-0,0-dimethyl phosphate, better known by the common name of DICHLORVOS or DDVP, the use of which in permanent insecticidal devices, so-called evaporators, has risen very greatly during recent years.

Various methods of stabilisation of the sensitive phosphoric esters in the evaporator have already been suggested to limit the decomposition of there phosphoric esters, but they are generally toxic such as phenols, amines or low nitrogen heterocyclics; another class of useful stabilizers includes azoic and hydrazonic compounds, but these possess a strong colouring ability which does not always permit them to be used. The use of anhydrides or epoxides has also been suggested, but it is known that these compounds act by fixation either of a molecule of water or of a molecule of free acid: it is clear that this process is stoichiometrically limited and that stabilisation ceases when all the stabiliser has reacted. This leads to the necessity of using substantial proportions of these stabilisers, which is not economic.

OBJECT AND SUMMARY OF THE INVENTION

It is an object of the present invention to stabilise volatile pesticidal phosphoric esters in an evaporator, by using substances more efficacious and not having the disadvantages stated above.

Certain benzodioxole derivatives have been suggested as insecticidal synergists, i.e. as reinforcing agents for the insecticidal action on contact with the insects, these being at very high concentrations of the order of 200 to 500% taken on the basis of the total weight of insecticidal compound. It has never been found, before the present invention, that the benzodioxole derivatives, particularly at low concentrations, are useful for preserving phosphoric esters present in evaporators against the protonisation occuring during stocking and use.

This invention accordingly provides an insecticide evaporator comprising:
I. (A). a solid or liquid insecticidal composition containing an insecticidally effective amount of a volatile insecticidal phosphoric ester selected from a di ($C_1$-$C_3$ alkyl)-dihalogenomethyl-vinyl-phosphate and a tetrahalogeno ($C_2$ or $C_3$ alkyl) di ($C_1$ or $C_2$ alkyl) phosphate, wherein the halogen substituents are chlorine or bromine, from about 0.2 to 20%, based on the weight of the volatile phosphoric ester, of a stabilising agent consisting essentially of
    B. about 0.1 to 10%, based on the weight of the volatile phosphoric ester, an 1,3-benzodioxole and
    C. about 0.1 to 10%, based on the weight of the volatile phosphoric ester of a diazene, and (II). a solid fibrous support absorbent for the composition (I). This evaporator may optionally comprise a solvent for the phosphoric ester, which may be solid or liquid, under pressure or otherwise. It may also optionally comprise one or more inert mineral or organic adjuvants.

According to the present invention the diazenes are those defined in U.S. application Ser. No. 17,918 filed Mar. 11, 1970, now abandoned in favour of the U.S. continuation-in-part application Ser. No. 427,103 filed Dec. 21, 1973 and now U.S. Pat. No. 3,966,900.

According to a preferred embodiment, the present invention concerns an insecticide evaporator comprising:
I. a solid or liquid insecticidal composition containing
   A. an insecticidally effective amount of insecticidal phosphate selected from the group consisting of
    2,2-dichloro vinyl dimethyl phosphate
    2,2-dichloro vinyl diethyl phosphate
    2,2-dichloro vinyl dipropyl phosphate
    2,2-dibromo vinyl dimethyl phosphate
    2,2-dibromo vinyl diethyl phosphate
    2,2-dibromo vinyl dipropyl phosphate
    2-bromo-2-chloro vinyl dimethyl phosphate
    2-bromo-2-chloro vinyl diethyl phosphate
    2,2-dichloro vinyl ethyl methyl phosphate
    2,2-dichloro 1-methyl vinyl dimethyl phosphate and
    2,2-dichloro 1-methyl vinyl diethyl phosphate,
wherein on contact with molecules of water at least partial decomposition of the ester takes place by protonization, said vinyl phosphate optionally being admixed with a solid or liquid solvent,
   B. about 0.1 to 10%, based on the weight of said volatile phosphate, of a 1,3-benzodioxole capable of stabilizing said phosphate against decomposition by protonization, said benzodioxole having no action as a toxicity synergist for the insecticidal phosphate in said proportions, and selected from the group consisting of at least one compound of the formula

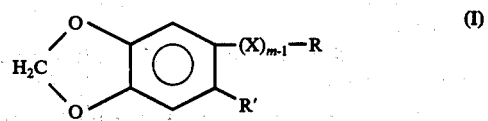

(I)

wherein m is 1 or 2, and X is an alkylene bridge of 1 or 2 or an alkenylene bridge of 2 carbon atoms, and R' is a. hydrogen or
b. lower alkyl and (A. When m represents 1 in formula (I) R represents)
a. hydrogen
b. lower alkyl
c. lower alkyenyl
d. halogen of atomic number not exceeding 17
e. nitro
f. the group

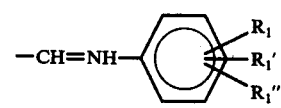

in which each of $R_1$, $R_1'$ and $R_1''$, independently of the others, is the same or a different group selected from the group consisting of hydrogen, lower alkyl, lower alkoxy, chloro and bromo;
g. the group

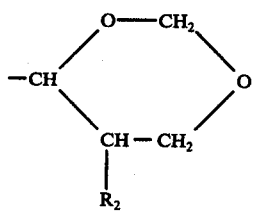

in which
$R_2$ is hydrogen or lower alkyl, or
h. the group

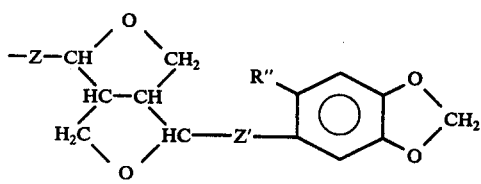

in which
Z and Z' are each independently a C-C bond or an oxygen atom (-O-) and R'' is hydrogen, lower alkyl or lower alkoxy, and
B. when m represents 1 or 2 in formula (I) R represents
i. cyano

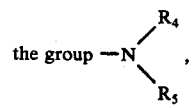

wherein
$R_4$ is hydrogen, lower alkyl and $R_5$ is hydrogen or lower alkyl,
iii. the group —CO—$R_6$ in which $R_6$ is
a. hydrogen b. -OM in which M is hydrogen or an equivalent metal cation or cation of a quaternary ammonium
c. lower alkyl or
d. lower alkoxy
e. phenyl, unsubstituted or substituted by one or more of the following substituents: lower alkyl, lower alkoxy, chloro, bromo;

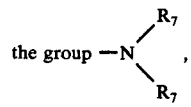

wherein each of
$R_7$ and $R_7'$ is independently selected from hydrogen or lower alkoxy

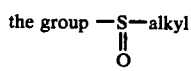

in which the alkyl group has 1 to 8 carbon atoms
v. the group -O-$R_8$
in which $R_8$ is lower alkyl or oxa alkyl of at most 15 carbon atoms and 3 oxygen atoms in the chain,

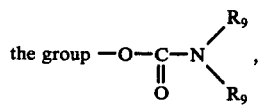

in which each of $R_9$ and $R_9'$ independently is hydrogen, lower alkyl or phenyl or
vii. nitro
C. when m represents 1 in formula (I):
R and R' taken together represent one of the following divalent groups:
a. the group

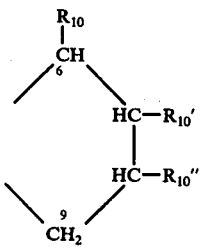

in which each of $R_{10}$, $R_{10}'$ and $R_{10}''$ independently is hydrogen, lower alkyl, alkoxycarbonyl of 2 to 5 carbon atoms, or the group -COOM, M having the meaning given above, or
b. the group

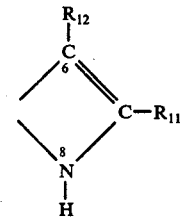

in which
$R_{11}$ is
hydrogen, lower alkyl, lower alkoxy or pyrrolidino, and
R$_{12}$ represents
hydrogen or lower alkyl, C. about 0.1 to 10% by weight based on the weight of said vinyl phosphate of at least one secondary agent for stabilizing said phosphate against decomposition by protonization selected from the group consisting of at least one diazene compound of the formula:

$$R - N = N - ZH \qquad (II)$$

or of its corresponding tautomeric hydrazonic formula:
, R — NH — N = Z
wherein ZH is a member selected from the group consisting of

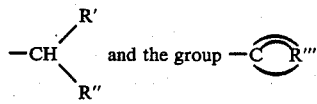

and Z the corresponding tautomeric divalent groups and R, R', R" and R'" having the following meanings: R represents a radical of hydroaromatic or of aromatic character comprising one, two or three rings, each having 5 or 6 ring members and when said radical contains two or three rings, the rings are condensed together or bound to each other, directly or via an oxygen atom or an —NH—, —CH$_2$—, or
— CH = CH —
group and when said radical represents three rings, the latter can form a triphenyl methan group; the radical R being selected from the group consisting of a. carbocyclic radicals of aromatic character having one to three rings and heterocyclic radicals of aromatic character having from one to three rings one of which contains one or two ring hetero atoms chosen from nitrogen, oxygen and sulphur;

b. carbocyclic or heterocyclic radicals with hydroaromatic character having two or three carbocyclic rings each of 5 or 6 ring members and at least two of these rings are condensed together, wherein two or four carbon atoms in one of the rings are saturated and at least one other ring is aromatic;

c. radicals as defined under (a) or (b) substituted by at least one member selected from the group consisting of one or two phenylazo, naphthylazo or arylazoarylazo, in which each of the aryl radicals is phenyl or naphthyl, or 4-pyrazolyl-azo groups; and d. a radical as defined under (a), (b), or (c) with at least one of its rings bearing one to four substituents selected from fluorine, chlorine, bromine, iodine, keto oxygen, hydroxy, carboxy, alkyl having from one to six carbon atoms, alkylene having from two or five carbon atoms, cycloalkyl having five or six carbon atoms, amino, alkanoylamino having up to five carbon atoms, mono-benzoylamino, alkoxy having from one to five carbon atoms, benzyloxy, nitro, sulpho, cyano, carbamoyl, benzoyl, amino substituted by one or two groups selected from the group consisting of alkyl groups having one to four carbon atoms, phenyl groups and benzyl groups, alkoxycarbonyl having from two to six carbon atoms, alkylsulphonyl having from one to five carbon atoms, sulphamoyl, the nitrogen atom of which is unsubstituted or substituted by one or two hydrocarbon radicals having a total of one to eight carbon atoms, alkanoyloxy having at most eighteen carbon atoms, and alkenoyloxy having at most eighteen carbon atoms, alkanoyl having up to five carbon atoms, and dialkylamino-alkyl having a total of from three to nine carbon atoms; and R' is a member selected from the group consisting of benzyl, alkyl of from one to seventeen carbon atoms, alkenyl of two to eight carbon atoms and a radical R as defined under any one of (a) to (d) as defined above and R" is a member selected from the group consisting of a radical R' as defined above, an unsubstituted phenylazo or naphthylazo group and a phenylazo or naphthylazo group substituted by methyl or ethyl; or R' R" taken together represent a divalent hydrocarbon radical having a total of four to fourteen carbon atoms which is a straight or branched chain radical or a chain radical containing an aryl ring condensed to the chain, any substituent of said hydrocarbon radical being selected from the substituents defined under (d), and groups of the formula =NX, in which X represents hydrogen, alkyl having from one to five carbon atoms or phenyl, and the group of formula:

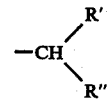

represents a radical R as defined under (a) to (d) above other than a group

as defined above wherein R' and R" are taken together, or (ii) a salt of a compound as defined under (i) above being at least one group capable of salt formation or, (iii) a metal complex of a compound or salt as defined under (i) or (ii) bearing one two groups capable of metal complex formation selected from hydroxy, carboxy, amino, mono (C$_1$-C$_4$ alkyl) amino, phenylamino, phenylsulphonamino and (C$_1$-C$_4$ alkyl) sulphonamido groups, said diazene being soluble in said composition, II. a solid fibrous support absorbent for the composition (I) formed by a felt of wool, a cellulosic fiber material or a cardboard of glass fibers.

The evaporators according to the invention may include a further stabilizing agent for said phosphoric ester which can be selected from elemental sulphur, compounds of divalent sulphur such as those defined in U.S. Pat. Nos. 3,832,464 and 3,836,643 and from epoxidised compounds.

The second stabilising agent (C) augments the stabilising effect of the principal agent (B) in a fashion showing a pronounced synergistic stabilisation action.

According to a preferred embodiment of the invention, the proportion of an epoxidized compound present ranges from about 0.1 to 20%, the proportion of a compound of divalent sulphur ranges from about 0.05 to 10% and the proportion of elemental sulphur from about 0.05 to 6%, all percentages being on the weight of the said volatile phosphoric ester.

When the insecticide evaporator is constituted by an impregnated support, the latter can be envelopped in a permeable membrane consisting of a layer of polyethylene or polypropylene or a mixture thereof, or of a copolymer of ethylene and propylene, or of a copolymer comprising vinyulidene chloride.

According to a preferred embodiment of the invention, the said permeable membrane is constituted by a layer of polyethylene having a thickness of from about 10 to 80 microns.

In preferred evaporators according to the invention, the stabilising agent (B) essentially consists of a mixture of a benzodioxole substituted by an unsaturated aliphatic group.

According to a preferred embodiment, the total proportion of stabilising agent is between 0.5 and 6% based on the weight of phosphoric ester. In the proportions suggested in the present invention, the benzodioxole has no action as toxicity synergist for the insecticidal phosphoric ester.

The organic constituents noted above for formula I and qualified above and in what follows, and in the claims, by the term "lower" have at most 6 carbon atoms and preferably 1 to 4 carbon atoms.

Included also within the benzodioxoles of formula I are the more or less volatile addition salts formed between benzodioxoles having a basic function and suitable organic or mineral acids. The term metallic ion, used in defining M above, includes ammonium ions $NR_wR_xR_yR_z$ in which $R_w$, $R_x$, $R_y$ and $R_z$ each independently represent hydrogen or an organic group, chiefly lower alkyl.

The term benzodioxole used in the following examples and claims always means 1,3-benzodioxole.

Particularly preferred benzodioxoles among those defined by formula I above, are chosen from the following classes:

1. *Simple benzodioxoles* defined by formula I'

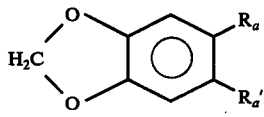

wherein $R_a$ is chosen from:

hydrogen, fluorine, bromine, alkyl of 1 to 6 carbon atoms, unsubstituted or substituted by nitro or phenyl, alkenyl of 2 to 4 carbon atoms, nitroalkenyl of 2 to 4 carbon atoms, styryl and nitro, and $R_a'$ is chosen from:

hydrogen, fluorine, chlorine, bromine and alkyl of 1 to 6 carbon atoms.

Such compounds are, for example, the following:

a. 5-nitro benzodioxole
c. 5-fluoro benzodioxole
d. 5-chloro benzodioxole
e. 5-bromo benzodioxole
f. 5,6-dichloro benzodioxole
g. 5,6-dibromo benzodioxole
h. 5-methyl benzodioxole
i. 5-propyl benzodioxole
j. 5-isobutyl benzodioxole
k. 5-tertbutyl benzodioxole
l. 5-hexyl benzodioxole
m. 5-methyl 6-propyl benzodioxole
n. 5,6-dimethyl benzodioxole
o. 5-(2-nitro propyl) benzodioxole
p. 5-vinyl benzodioxole
q. 5-allyl benzodioxole
r. 5-(propen-1-yl) benzodioxole
s. 5-methallyl benzodioxole
t. 5-allyl 6-methyl benzodioxole
u. 5-allyl 6-butyl benzodioxole
v. 5-styryl benzodioxole
w. 5-(2-nitro vinyl) benzodioxole
x. 5-(2-nitro propen-1-yl) benzodioxole
y. 5-benzyl benzodioxole;

2. *Carbonylated benzodioxoles* defined by formula II'

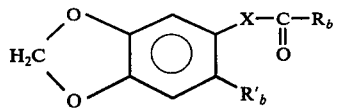

in which X is a direct bond or is an alkylene or alkenylen groups, each of which contains at most 7 carbon atoms in straight or branched chain; $R_6{}^b$ is hydrogen or alkyl of 1 to 4 carbon atoms or phenyl optionally substituted by one or two low alkyl groups, or a carbamoyl group optionally substituted by one or two low alkyl groups or phenyl, and $R_6{}^{b'}$ represents hydrogen, low alkyl, chlorine, bromine, fluorine or nitro. Such compounds are, for example, the following:

a. 5-formyl benzodioxole
b. 5-chloro 6-formyl benzodioxole
c. 5-formyl 6-nitro benzodioxole
d. 5-(2-formyl vinyl) benzodioxole
e. 5-acetyl benzodioxole
f. 5-acetyl 6-methyl benzodioxole
g. 5-propionyl benzodioxole
h. 5-benzoyl benzodioxole
i. 5-butyryl benzodioxole
j. 5-(2-carbamoyl ethyl) benzodioxole
k. 5-(2-N-methylcarbamoyl ethyl) benzodioxole
l. 5-(3-N-methylcarbamoyl propyl) benzodioxole
m. 5-(1-N-methylcarbamoyl 2-propyl) benzodioxole
n. 5-(2-N-butylcarbamoyl ethyl) benzodioxole
o. 5-(2-N,N-dimethylcarbamoyl ethyl ) benzodioxole
p. 5-(2-N-phenylcarbamoyl ethyl) benzodioxole
q. 5-(2-N,N-diphenylcarbamoyl ethyl) benzodioxole
r. 5-(2-oxo propyl) benzodioxole
s. 5-(3-oxo butyl) benzodioxole
t. 5-(2-oxo butyl) benzodioxole
u. 5-(2-oxo pentyl) benzodioxole
v. 5-[2-(4-methyl benzoyl) vinyl] benzodioxole
w. 5-(2-oxo hexyl) benzodioxole
x. 5-benzoylmethyl benzodioxole
y. 5-(3-oxo butene-1 yl) benzodioxole
z. 5-(4-methyl benzoyl)methyl benzodioxole
a'. 5-(3-oxo-2-methyl butene-1 yl) benzodioxole
b'. 5-(2,4-dimethyl benzoyl)methyl benzoxioxole
c'. 5-(3-oxo 2-methyl pentene-1 yl) benzodioxole
d'. 5-(4-ethyl benzoyl)methyl benzodioxole
e'. 5-(3-oxo 2-pentyl butene-1 yl) benzodioxole
f'. 5-(3-oxo 2-ethyl butene-1 yl) benzodioxole
g'. 5-(2-benzoyl ethyl) benzodioxole
h'. 5-(3-benzoyl propyl) benzodioxole
i'. 5-(3-oxo 2-isopropyl butene-1 yl) benzodioxole
j'. 5-(2-benzoyl vinyl) benzodioxole
k'. 5-(3-acetyl 2,2-diethyl propyl) benzodioxole
l'. 5-(2-formyl ethyl) benzodioxole
m'. 5-[2- (2,4-dichloro benzoyl) ethyl ] benzodioxole
n'. 5 [ 2-(4-bromo benzoyl) ethyl ] benzodioxole
n'. 5-(7-acetyl heptyl) benzodioxole 3. *Carboxylated benzodioxoles* defined by formula III

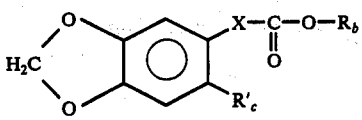

in which X and $R_b'$ are as defined in 2) above, and $R_c$ is hydrogen, alkyl of 1 to 4 carbon atoms or low alkenyl, or an oxa-alkyl group containing 3 to 7 carbon atoms or a dioxa-alkyl group containing 5 to 10 carbon atoms, or a phenyl group. Such compounds are, for example, the following:

a. 5-carboxy benzodioxole
b. 5-methyloxycarbonyl benzodioxole
c. 5-ethoxycarbonyl benzodioxole
d. 5-butoxy carbonyl benzodioxole
e. 5-(2-ethoxy ethoxy)carbonyl benzodioxole
f. 5-(3,6-dioxa decyl) oxycarbonyl benzodioxole
g. 5-(2-carboxy vinyl) benzodioxole
h. 5-(2-carboxy ethyl) benzodioxole
i. 5-(2-carboxy hepten-1 yl) benzodioxole
k. 5-(2-methoxycarbonyl vinyl) benzodioxole
l. 5-(2-butoxy carbonyl vinyl) benzodioxole
m. 5-(2-carboxy vinyl) 6-nitro benzodioxole
n. 5-carboxy 6-nitro benzodioxole
o. 5- ethoxycarbonyl 6-nitro benzodioxole
p. 5-(carboxymethyl) benzodioxole
q. 5-(4-carboxy butadien-1,3 yl) benzodioxole
r. 5-carboxy 6-chloro benzodioxole
s. 5-ethoxycarbonyl 6-methyl benzodioxole
t. 5-phenoxycarbonyl benzodioxole
u. 5-(phenoxycarbonyl-methyl) benzodioxole
v. 5 -allyloxycarbonyl benzodioxole.

4. Nitrilated benzodioxoles defined by formula IV

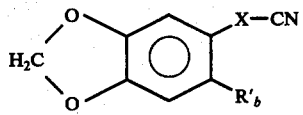

in which X and $R_b'$ are as defined in 2) above. Such compounds are, for example
a. 5-cyano benzodioxole
b. 5-cyano 6-nitro benzodioxole
c. 5-dyanomethyl benzodioxole
d. 5-(2-cyano ethyl) benzodioxole
e. 5-(2-cyano vinyl) benzodioxole
f. 5-(2-cyano vinyl) 6-nitro benzodioxole
g. 5-(2-cyano hepten-1 yl) benzodioxole
h. 5-(5-cyano pentyl) benzodioxole
i. 5-(2-cyano heptyl) benzodioxole
j. 5-cyano 6-chloro benzodioxole
k. 5-cyanomethyl 6-methyl benzodioxole.

5. Hydroxylated benzodioxoles of formula V.

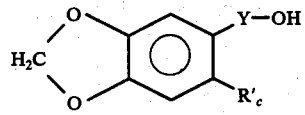

in which Y is a direct bond or is alkylene of 1 to 4 carbon atom in straight or branched chain, or is low alkenylene, and $R_c$ is hydroben, methyl, bromine or chlorine. Such compounds are, for example:

a. 5-hydroxy benzodioxole
b. 5-hydroxymethyl benzodioxole
c. 5-(hydroxy-2 ethyl) benzodioxole
d. 5-(hydroxy ethyl) benzodioxole
e. 5-(3 hydroxy propyl) benzodioxole
f. 5-(1-hydroxy propyl) benzodioxole
g. 5-(1-hydroxy butyl) benzodioxole
h. 6-chloro 5-hydroxymethyl benzodioxole
i. 5-hydroxy 6 methyl benzodioxole
j. 5-hydroxymethyl 6-methyl benzodioxole
k. 5-hydroxy 6-bromo benzodioxole
l. 5-(3-hydroxy butene-1 yl) benzodioxole.

6. Aminated benzodioxoles defined by formula VI.

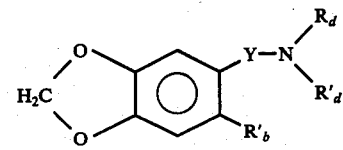

wherein $R_b'$ and Y are as defined in 2) and 5) above respectively, and $R_d$ and $R_d'$ are the same or different and are each hydrogen or alkyl of 1 to 4 carbon atoms, or one of them can be alkanoyl of 1 to 4 carbon atoms, and also $R_d$ and $R_d'$ can represent, together with the nitrogen atom to which they are attached, pyrrolidino, piperidino, morpholino or azepino. Such compounds are, for example, the following:

a. 5-(N,N-dimethylamino) benzodioxole
b. 5-(N,N-dimethylaminomethyl) benzodioxole
c. 5-(2-amino propyl) benzodioxole
d. 5-(N-formyl N-methyl aminomethyl) benzodioxole
e. 5-(N-acetylaminomethyl) benzodioxole
f. 5-(2-N-butyrylamino propyl) benzodioxole
g. 5-(2-N-methylamino ethyl) benzodioxole
h. 5-(2-N,N-diethylamino butyl) benzodioxole
i. 5-(2-N,N-dibutylamino ethyl) benzodioxole
j. 5-piperidinomethyl benzodioxole
k. 5-(1-azepinyl methyl) benzodioxole
l. 5-(2-morpholino ethyl) benzodioxole
m. 5-(4-methyl piperidino) methyl benzolioxole
n. 5-(2-pyrrolidino ethyl) benzodioxole
o. 5-aminomethyl 6-nitro benzodioxole
p. 5-(2-amino propyl) 6-nitro benzodioxole
q. 5-N,N-dimethylaminomethyl) 6-nitro benzodioxole
r. 5-piperidino benzodioxole
s. 5-(3-N,N-dimethlamino butene-1 yl) benzodioxole
t. 5-(2-N-methylamino ethyl) 6-isopropyl benzodioxole
u. 5-(2-amino propyl) 6-methylbenzodioxole
v. 5-(2-amino propyl) 6-chloro benzodioxole.

7. Benzodioxoles having a sulphoxide function defined by formula VII

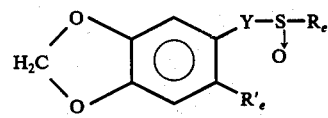

wherein Y is as defined in 5) above, but is preferably an alkylene bridge, $R_e$ is alkyl of 1 to 8 carbon atoms and $R_e'$ is hydrogen or alkyl of 1 to 4 carbon atoms. Such compounds are, for example, the following:
a. 5-(2-methylsulfinyl butyl) benzodioxole
b. 5-(2-butylsulfinyl ethyl) benzodioxole c. 5-(2-butylsulfinyl propyl) benzodioxole
d. 5-(2-octyl sulfinyl propyl) benzodioxole
e. 5-(2-octylsulfinyl ethyl) benzodioxole
f. 5-(3-octylsulfinyl propyl) benzodioxole
g. 6-methyl 5-(2-octylsulfinyl propyl) benzodioxole
h. 6-propyl 5-(2-octylsulfinyl propyl) benzodioxole
i. 6-butyl 5-(2-octylsulfinyl propyl) benzodioxole
j. 5-(2-octylsulfinyl ethyl 6-chloro) benzodioxole;

8. Benzodioxoles having at least-one ether group defined by formula VIII

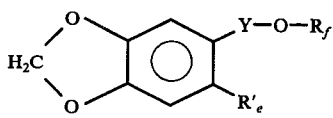
VIII in which Y and $R_e'$ are as defined in 5) and 7) above respectively, and $R_f$ is alkyl of 1 to 4 carbon atoms or alkoxyalkyl of 2 to 7 carbon atoms, or alkoxyalkoxy-alkyl of 4 to 10 carbon atoms, or alkoxyalkoxy alkyl of 5 to 15 carbon atoms, or phenyl. Such compositions are, for example, the following:

a. 5-methoxy benzodioxole
b. 5-butoxy benzodioxole
c. 5-(2-ethoxy ethoxy) benzodioxole
d. 5-(2-ethoxy methyl) benzodioxole
e. 5-(2-methoxy propyl) benzodioxole
f. 5-(2-butoxy butyl) benzodioxole
g. 5-(2,5,8-trioxa dodecyl) benzodioxole
h. 5-methyl 6-(2,5,8-trioxa dodecyl) benzodioxole
j. 5-propyl 6-(2,5,8-trioxa dodecyl) benzodioxole
k. 6-chloro 5-ethoxymethyl benzodioxole
l. 5-(3-methoxy butene-1 yl) benzodioxole
m. 5-phenoxymethyl benzodioxole
n. 5-ethoxy 6-nitro benzodioxole
o. 5-(3,6,9-trioxa undecyl-2) oxy benzodioxole
p. 6-ethyl 5-(3,6,9-trioxa undecyl-2) oxy benzodioxole 9. Benzodioxoles having an acetal function defined by formula IX

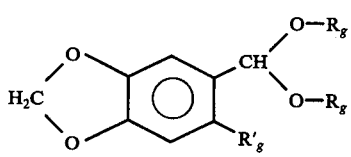
IX in which
$R_g$ is an alkyl group of 1 to 4 carbon atoms, or alkoxy alkyl of 2 to 7 carbon atoms or alkoxyalkoxy alkyl of 4 to 10 carbon atoms, and
$R'_g$ is hydrogen, chlorine, bromine, fluorine, nitro or lower alkyl. Such compounds are, for example:

a. 5-(dimethoxy)methyl benzodioxole
b. 5-(diisobutoxy) methyl benzodioxole
c. 5-bis(2-ethoxy ethoxy) methyl benzodioxole
d. 5-bis (2-butoxy ethoxy) methyl benzodioxole
e. 5-bis (2-butoxy propoxy) methyl benzodioxole
f. 5-bis(3,6-dioxy decyloxy) methyl benzodioxole
g. 5-bis(5-methyl 4,7-dioxa dodecyloxy)methyl benzodioxole
h. 5-(dipropyloxy)methyl benzodioxole
i. 5-(dipropyloxy)methyl 6-chloro benzodioxole
j. 5-(dipropyloxy)methyl 6-nitro benzodioxole
k. 5-(dipropyloxy)methyl 6-methyl benzodioxole;

10. Benzodioxoles having a carbonic function defined by formula X

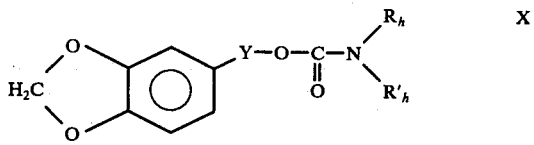
X in which Y is as defined in 5) above, and $R_h$ and $R_h'$ are the same or different and are each hydrogen or alkyl of 1 to 4 carbon atoms, or are, together with the nitrogen atoms, piperidino, morpholino or pyrrolidino. Such compounds are, for example, as follows:

a. 5-carbamoyl oxy benzodioxole
b. 5-(N-methylcarbamoyl oxy) benzodioxole
c. 5-(N-butylcarbamoyl oxy) benzodioxole
d. 5-(N,N-dipropylcarbamoyl oxy) benzodioxole
e. 5-(N,N-pentamethylene carbamoyl oxy) benzodioxole
f. 5-carbamoyl oxy methyl benzodioxole
g. 5-(N,N-dimethylcarbamoyl oxy ethyl) benzodioxole
h. 5-(2-N,N-diethylcarbamoyl oxy ethyl) benzodioxole
i. 5-(2-N-butylcarbamoyl oxy butyl) benzodioxole
j. 5-(2-N,N-tetramethylene carbamoyl oxy propyl) benzodioxole
k. 5-(3-N-methylcarbamoyloxy butene-1 yl) benzodioxole
l. 5-morpholinocarbamoyloxymethyl benzodioxole
m. 5-N-isopropylcarbamoyloxy 6-methyl benzodioxole
n. 5-N-propylcarbamoyloxy 6-nitro benzodioxole
o. 5-N-ethylcarbamoyloxy 6-chloro benzodioxole
p. 5-piperidinocarbonyloxy benzodioxole;

11. Benzodioxoles carrying a dioxane ring defined by formula XI

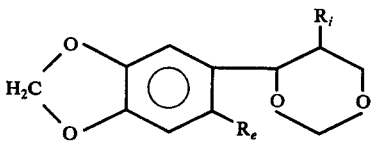
XI in which $R_e'$ is as defined in 7) above and $R_i$ is hydrogen, methyl or ethyl. Such compounds are, for example:

a. 5-(4-dioxane-1,3 yl-4) benzodioxole
b. 5-(4-dioxane-1,3 yl-4) 6-methyl benzodioxole
c. 5-(4-dioxane-1,3 yl-4) 6-propyl benzodioxole
d. 5-[(4-)5-methyl dioxane-1,3 yl)] benzodioxole
e. 5-[(4-)5-methyl dioxane-1,3 yl)] 6-propyl benzodioxole
f. 5-[(4-)5-ethyl dioxane-1,3 yl)] benzodioxole;

12. Benzodioxole derivatives of tetraline defined by formula XII

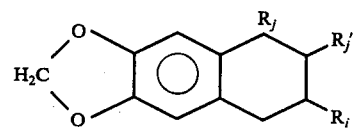
XII in which $R_i$ is as defined in 11) above, and $R_j$ and $R_j'$ are the same or different and are each hydrogen, methyl, carboxy or alkoxycarbonyl containing in total 2 to 5 carbon atoms. Such compounds are for example:

a. 5,6,7,8-tetrahydro naphtho-(2,3-d) 1,3-dioxole
b. 5,6,7-trimethyl 5,6,7,8-tetrahydro naphtho-(2,3-d) 1,3-dioxole
c. 6,7-dimethyl 5,6,7,8-tetrahydro naphtho (2,3-d) 1,3-dioxole
d. 5,6-dicarboxy 5,6,7,8-tetrahydro naphtho (2,3-d) 1,3-dioxole
e. 5,6-dicarboxy 7-methyl 5,6,7,8-tetrahydro naphtho (1,3-d) 1,3-dioxole
f. 5,6-bis(ethoxy-carbonyl) 7-methyl 5,6,7,8-tetrahydro naphtho (2,3-d) 1,3-dioxole
g. 5,6-bis(propoxycarbonyl) 7-methyl 5,6,7,8-tetrahydro naphtho (2,3-d) 1,3-dioxole
h. 5,6-bis(butoxycarbonyl) 7-ethyl 5,6,7,8-tetrahydro naphtho (2,3-d) 1,3-dioxole;

13. Benzodioxole derivatives of dioxabicyclooctane defined by formula XIII

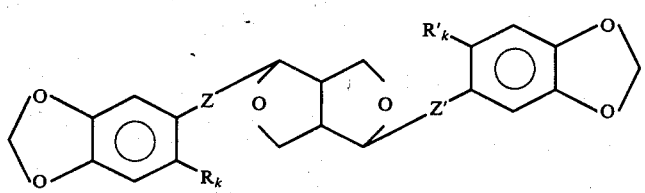

XIII in which Z and Z' are the same or different and are each a direct bond or an oxygen atom; $R_k$ and $R_k'$ are the same or different and are hydrogen, methyl or methoxy. Such compounds are, for example:
a. 2,6-bis(5-benzodioxole-1,3 yl 3,7-dioxa bicyclo (3,30) octane
b. 2,6-bis(5-benzodioxole-1,3 yl oxy) 3,7-dioxa bicyclo (3,3,0) octane
c. 2-(5-benzodioxole-1,3 yl) 6-(5-benzodioxole-1,3 yl oxy) 3,7-dioxabicyclo(3,3,0) octane
d. 2-(5-benzodioxole-1,3 yl) 6-(5-(6-methoxy benzodioxole-1,3 yl)) 3,7-dioxa bicyclo(3,3,0) octane
e. 2-(5-benzodioxole-1,3 yl)6-(5-methyl-6 benzodioxole-1,3 yl)) 3,7-dioxa bicyclo(3,3,0)octane
f. 2,6-bis (5-(6-methoxy benzodioxole-1,3 yl)) 3,7-dioxa bicyclo (3,3,0) octane
g. 2,6-bis (5-(6-methyl benzodioxole-b 1,3 yl)) 3,7-dioxa bicyclo (3,3,0) octane;

14. Benzodioxole derivatives of indole defined by formula XIV

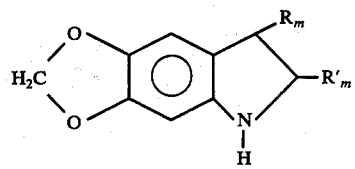

XIV in which $R_m$ is hydrogen, alkyl of 1 to 4 carbon atoms or alkoxy of 1 to 4 carbon atoms, each of these groups optionally bearing a group

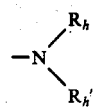

as defined in 10) above, $R_m'$ is hydrogen, alkyl of 1 to 4 carbon atoms, alkoxy of 1 to 4 carbon atoms, alkanoyl of 2 to 4 carbon atoms or benzoyl. Such compounds are, for example, the following
a. (1,3 dioxolo) [4,5-f]indole
b. 3-methyl (1,3 dioxolo) [4,5-f] indole
c. 3-ethyl (1,3 dioxolo) [4,5-f] indole
d. 3-butyl (1,3 dioxolo) [4,5-f] indole
e. 2,3-dimethyl (1,3 dioxolo) [4,5-f] indole
f. 3-methoxy (1,3 dioxolo) [4,5-f] indole
g. 3-isobutoxy (1,3 dioxolo) [4,5-f] indole
h. 2,3-dimethoxy (1,3 dioxolo) [4,5-f] indole
i. 2-ethyl 3-methoxy (1,3 dioxolo) [4,5-f] indole
j. 3-(2-N,N-dimethylamino ethyl) (1,3 dioxolo) [4,5-f] indole
k. 3-(3-N-ethylamino propyl) (1,3 dioxolo) [4,5-f] indole
l. 3-(2-amino ethoxy) (1,3 dioxolo) [4,5-f] indole
m. 3-(2-N,N-diethylamino ethoxy) (1,3 dioxolo) [4,5-f] indole
n. 3-(2-pyrrolidino ethoxy) (1,3 dioxolo) [4,5-f] indole
o. 3-(2-piperidino ethoxy) (1,3 dioxolo) [4,5-f] indole
p. 2-acetyl 3-(2-pyrrolidino ethoxy) (1,3 dioxolo) [4,5-f] indole
q. 2-butyryl 3-(2-pyrrolidino ethoxy) (1,3 dioxolo) [4,5-f] indole
r. 3-benzoyl 3-(2-pyrrolidino ethoxy) (1,3 dioxolo) [4,5-f] indole;

15. Benzodioxoles carying an imine function defined by formula XV

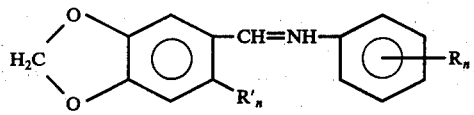

in which $R_n$ represents one to three substituents optionally chosen from alkyl of 1 to 4 carbon atoms, alkoxy of 1 to 4 carbon atoms, chloro, bromo, nitro, hydroxy and methyl thio. Such compounds are, for example, the following anilines N-substituted by piperonylidene.
a. aniline
b. 4-methyl aniline
c. 4-butyl aniline
d. 2,4-dimethyl aniline
e. 4-methoxy aniline
f. 2,4-dimethoxy aniline
g. 2,4,6-trimethoxy aniline
h. 4-butoxy aniline
i. 3-nitro aniline
j. 5-chloro 2,4-dimethoxy aniline
k. 2-chloro aniline
l. 2,3-dichloro aniline
m. 4-chloro 2-methyl aniline
n. 3-methylthio aniline
o. 2-bromo 4-nitro aniline
p. 2-hydroxy aniline
q. 5-chloro 2-methyl aniline
r. 4-bromo aniline
s. 2,5-dichloro aniline t. 2,3,5-trichloro aniline
u. 2,4,6-trimethyl aniline
v. 4-t-butyl aniline and the following anilines
x. N-(3'-chloro piperonylidene)-aniline
y. N-(3'-methyl piperonylidene)-(4-methyl aniline)
z. N-(3'-nitro piperonylidene)-(3-nitro aniline); 16. Salt derivatives of benzodioxoles, having an acid or phenolic function defined in 3), 5) and 12) above, these salts containing as cation a metal such as sodium, potassium, calcium, zinc, cadmium, copper, nickel, cobalt, iron, manganese, silver, lead, barium, strontium and aluminium, or an ammonium ion derived from ammonia, an amine derivative containing 1 to 3 alkyl groups and 1 to 4 carbon atoms, for example methylamine, dimethylamine, trimethylamine, diethylamine, triethylamine, butylamine, dibutylamine and tributylamine, or a heterocyclic nitrogen derivative, e.g. pyridine, morpholine, N-methyl morpholine, piperidine and pipecolines.

Such salts are, for example, the following:

The sodium salts of compounds III (*a*), III (*g*), III (*n*), III (*r*) V (*a*), XII (*d*) and XII (*e*).

The ammonium salts of compounds III (*a*), III (*h*), III (*m*), III (*p*), V (*i*) and XII (*d*).

The neutral zinc salts of compounds III (*a*), V (*a*) and XII (*e*).

The use of these salts is of particular value when the phosphoric ester used has already undergone some protonisation; the salt introduced as stabiliser then acts as a first stage as a neutraliser for the acid phosphoric ester by exchanging its cation therewith for a portion; this neutralisation favours the stabilisation since it has been observed by the applicants that the preservation of phosphoric esters is better whem they do not contain any acid by-products; the benzodioxole, having lost its cation, keeps its stabilising properties and then acts for a second time.

17. Salt derivatives of benzodioxoles having a basic function defined in 6) and 14) above, these salts being formed with a mineral acid such as hydrochloric, sulphuric, carbonic, boric, hydrobromic or phosphoric acid, or an organic mono- or di- carboxylated acid such as acetic, propionic, benzoic, succinic, adipic, phthalic, maleic orphenylacetic acid. Such salts are, for example, the following:

a to o: the chloride, sulphate, carbonate, borate, bromide, hydrogenphosphate, dihydrogen phosphate, acetate, propionate, benzoate, succinate, adipate, phthalate, maleate and phenylacetate of 5-(N,N-dimethylamino)-benzodioxole (VI (*a*))

p to z and a' to d': the salts of the same acids as in a) to o) just noted of (1,3-dioxolo [4,5-f] indole (XIV(*a*);

The diazenes preferred for practical use according to the invention are chosen from the following classes:

—1° MONOAZO COMPOUNDS DEFINED BY THE FOLLOWING FORMULA:

wherein $R_a$ and $R'_a$ are the same or different and each represents phenyl, naphthyl, pyridyl, quinolyl or diphenyl; examples of such compounds are the following:
azobenzene
1-phenylazo-naphthalene
2-phenylazo-naphthalene
2,2'-azonaphthalene
1,1'-azonaphthalene
2,2'-azopyridine
2,2'-azoquinoline
o-azodiphenyl
p-azodiphenyl.

—2° MONO-AZO COMPOUNDS DEFINED BY THE FOLLOWING FORMULA:

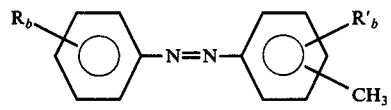

wherein $R_b$ represents hydrogen or one or two methyl radicals, $R'_b$ represents hydrogen or a methyl radical. Examples of such compounds are the following:
2-methyl-azobenzene
3-methyl-azobenzene
4-methyl-azobenzene
2,2'-dimethyl-azobenzene
3,3'-dimethyl-azobenzene
4,4'-dimethyl-azobenzene
2,2',3,3'-tetramethyl-azobenzene
3,3',4,4'-tetramethyl-azobenzene
2,2',4,4'-tetramethyl-azobenzene
3,3',5,5'-tetramethyl-azobenzene
2,2',5,5'-tetramethyl-azobenzene.

—3° MONO-AZO COMPOUNDS DEFINED BY THE FOLLOWING FORMULA:

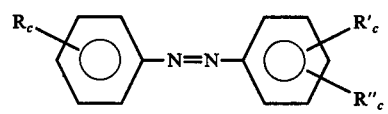

wherein $R_c$ represents hydrogen or one or two halogens, $R'_c$ represents halogen, and $R''_c$ represents hydrogen or halogen, halogen being chloride, bromine, fluorine or iodine. Examples of such compounds are the following:
2,2'-dichloro-azobenzene
3,3'-dichloro-azobenzene
4,4'-dichloro-azobenzene
4,4'-difluoro-azobenzene
2,2'-dibromo-azobenzene
4,4'-dibromo-azobenzene
4,4'-diiodo-azobenzene.

—4° MONO-AZO COMPOUNDS DEFINED BY THE FOLLOWING FORMULA:

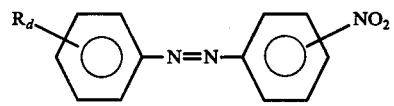

wherein $R_d$ represents hydrogen or a nitro group. Examples of such compounds are the following:
4-nitro-azobenzene
3,3'-dinitro-azobenzene
4,4'-dinitro-azobenzene.

—5° MONO-AZO AMINO COMPOUNDS DEFINED BY THE FOLLOWING FORMULA OR BY THE TAUTOMERIC FORMULA OF THE CORRESPONDING IMINOHYDRAZONE COMPOUNDS:

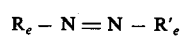

wherein $R_e$ represents a phenyl or naphthyl radical substituted by one or two amino groups which are optionally substituted by an acetyl or benzoyl radical, by one or two phenyl or benzyl radicals or by alkyl having 1 to 4 carbon atoms, the radical $R_e$ being optionally further substituted by one or three substituents chosen from alkyl radicals having 1 to 5 carbon atoms, chlorine, nitro, alkoxy groups having 1 to 3 carbon atoms, alkylsulfonyl groups having 1 to 4 carbon atoms and sulfamoyl groups, the latter being optionally N-substituted by one or two alkyl radicals having 1 to 4 carbon atoms; $R'_e$ represents a phenyl, naphthyl or pyrazolyl radical, optionally substituted by one to three substituents chosen from methoxy, ethoxy and propoxy groups, methyl, ethyl, phenyl and cyclohexyl radicals and chlorine, nitro and amine groups, the latter being optionally substituted by one or two phenyl, benzyl or alkyl radicals having 1 to 4 carbon atoms. Examples of such compounds are the following:

2-amino-azobenzene
3-amino-azobenzene
4-amino-azobenzene
3,3'-diamino-azobenzene
4,4'-diamino-azobenzene
1-phenylazo-4-amino-naphthalene
1-phenylazo-2-amino-naphthalene
1($\alpha$-naphthylazo)-4-amino-naphthalene
1-($\alpha$-naphthylazo)-2-amino-naphthalene
1-($\beta$-naphthylazo)-2-amino-naphthalene
4-phenylazo-m-phenylene-diamine
4-phenylozo-diphenylamine
4-(N,N-dimethylamino)-azobenzene
4-(N,N-diethylamino)-azobenzene
1-(2-methyl-phenylazo)-2-amino-naphthalene
4-($\alpha$-naphthylazo)-m-phenylene-diamine
4-phenylazo-m-toluylene-diamine
4-amino-4'-nitro-azobenzene
4-(N-benzylamine)-5'-chloro-4'-cyclohexyl-2'-methyl-azobenzene
1-(2-chloro-4-nitro-phenylazo)-2-amino-5-sulfamoyl-naphthalene
1-(2-chloro-4-nitro-phenylazo)-2-amino-5-(N-methyl-sulfamoyl)-naphthalene
2-(2-chloro-4-nitro-phenylazo)-5-diethylaminotoluene
4-(4-nitro-phenylazo)-3-acetylamino-aniline
4-(4-nitrophenylazo)-3-methyl-aniline
4-phenylazo-N-acetylaniline
1-(6-chloro-2,4-dinitro-phenylazo)-4-diethylaminonaphthalene
5-(2,4-dinitro-phenylazo)-4-acetylamino-2-(N-benzyl-N-ethyl-amino)-anisole
4-(2,4-dinitro-phenylazo)-5-amino-3-methyl-1-phenyl-pyrazole
4-(4-ethylsulfonyl-2-nitro-phenylazo)-5-amino-3-methyl-1-phenyl-pyrazole
1-(2-methoxy-4-nitro-phenylazo)-4-diethylaminotoluene.

—6° MONO-AZO COMPOUNDS, KNOWN AS OXYAZO COMPOUNDS DEFINED BY THE FOLLOWING FORMULA OR BY THE TAUTOMERIC FORMULA OF THE CORRESPONDING HYDRAZONOQUINONE COMPOUNDS:

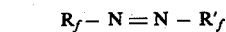

wherein $R_f$ represents a phenyl, naphthyl, or quinolyl radical having one or two hydroxy groups and optionally substituted by one to three further substituents chosen from chlorine, alkyl radicals containing 1 to 5 carbon atoms, the cyclohexyl radical, and carbamoyl, carboxyl and nitro groups; $R'_f$ represents a phenyl, naphthyl or pyridyl radical optionally further substituted by one to four substituents chosen from chlorine, the cyclohexyl radical, the methyl radical and the hydroxy, nitro, methoxy, benzyloxy, dimethylamino and dimethylaminomethyl groups. Examples of such compounds are the following:

4-hydroxy-azobenzene
2-hydroxy-azobenzene
2,2'-dihydroxy-azobenzene
3,3'-dihydroxy-azobenzene
4,4'-dihydroxy-azobenzene
3,4-dihydroxy-azobenzene
2,6-dihydroxy-azobenzene
2,5-dihydroxy-azobenzene
1-phenylazo-2-naphthol
4-phenylazo-1-naphthol
2-phenylazo-1-naphthol
2-($\alpha$-naphthylazo)-1-naphthol
1-($\alpha$-naphthylazo)-2-naphthol
1-($\beta$-naphthylazo)-2-naphthol
1-(2-pyridyl-azo)-2-naphthol
4-(4-nitro-phenylazo)-resorcinol
4-(4-nitro-phenylazo)-5-methyl-resorcinol
5-(4-nitro-phenylazo)-salicyclic acid
4-phenylazo-m-cresol
4-phenylazo-resorcinol
4-phenylazo-o-cresol
1-xylylazo-2-naphthol
1-(o-anisylazo)-2-naphthol
1-(p-anisylazo)-2-naphthol
1-(4-chloro-o-anisylazo)-2-naphthol
3-phenylazo-2,4-dihydroxy-quinoline
3-phenyl-2-hydroxy-quinoline
2,2',4-trihydroxy-5'-nitro-azobenzene
4-(N,N-dimethylamino-2-methyl-phenylazo)-resorcinol
2(2-benzyloxy-5-chloro-phenylazo)-3,6-disulfo-8-tolylsulfamido-1-naphthol
1-xylylazo-2-naphthol
1-(2-hydroxy-4-nitro-phenylazo)-2-naphthol
1(2-hydroxy-5sulfamoyl-phenylazo)-2-naphthol
1-(2-hydroxy-5-nitro-phenylazo)-2-naphthol
2-(4-cyclohexyl-2-methyl-phenylazo)-4-cyclohexyl-phenol
2-(4-cyclohexyl-2,5-dimethyl-phenylazo)-4-cyclohexyl-phenol
2-(4-cyclohexyl-2-methoxy-phenylazo)-4cyclohexyl-phenol
2-(4-cyclohexyl-2-methyl-phenylazo)-5,6,7,8-tetrahydro-2-naphthol (2,4-dichloro-phenylazo)-2-naphthol

—7° MONO-AZO COMPOUNDS DEFINED BY THE FOLLOWING FORMULA:

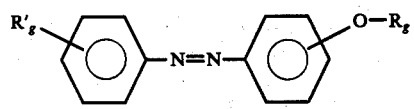

wherein $R_g$ represents an alkyl radical containing 1 to 4 carbon atoms or an alkanoyl radical containing 2 to 18 carbon atoms, $R'_g$ represents hydrogen or an alkoxy group containing 1 to 4 carbon atoms. Examples of such compounds are the following:
- 4,4'-azoanisole
- 4,4'-azophenetol
- 4-methoxy-azobenzene
- 4-ethoxy-azobenzene
- 2-acetoxy-azobenzene
- 2,2'-azophenetol
- 2,2'-azoanisole
- 4-butyroxy-azobenzene
- 4-heptanoyloxy-azobenzene
- 1-(4-ethoxy-phenylazo)-4-heptanoyloxy-benzene
- 4-palmitoyloxy-azobenzene
- 4-lauroyloxy-azobenzene.

—8° PHENYLHYDRAZONE COMPOUNDS DEFINED BY THE FOLLOWING FORMULA:

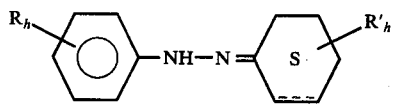

wherein $R_h$ represents hydrogen or one or two substituents chosen from chlorine and the nitro group; $R'_h$ represents hydrogen or one to three alkyl radicals having 1 to 4 carbon atoms; the dotted line represents an optical second bond. Examples of such compounds are the following:
- phenylhydrazonocyclohexane
- 4-chloro-phenylhydrazonocyclohexane
- 4-nitro-phenylhydrazonocyclohexane
- 1-phenylhydrazono-2-methyl-cyclohexane
- 1-phenylhydrazono-4-methyl-cyclohexane
- 1-phenylhydrazono-3,3,5-trimethyl-cyclohexane
- 1-phenylhydrazono-3,5,5-trimethyl-cyclohex-2-ene
- 2-phenylhydrazono-methane.

—9° PHENYLHYDRAZONE COMPOUNDS DEFINED BY THE FOLLOWING FORMULA OR BY THE TAUTOMERIC FORMULA OF THE CORRESPONDING HYDROXYAZO COMPOUNDS:

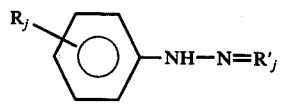

wherein $R_j$ represents one to three substituents chosen from alkyl radicals having 1 to 5 carbon atoms, chlorine, nitro, hydroxy, carboxy, sulfo and methylsulfonyl groups; $R'_j$ represents a 2-indolinon-3-ylidene or a 3,4-dihydro-3-pyrazolon-4-ylidene radical, optionally substituted by a methyl radical and/or a phenyl, chlorophenyl or sulfophenyl radical. Examples of such compounds are the following:
- 3-phenylhydrazono-2-inodolone
- 4-nitro-3-phenylhydrazono-2-indolone
- 3-(4-chloro-phenylhydrazono)-2-inodolone
- 4-phenylhydrazono-1-phenyl-3-methyl-4,5-dihydro-5-pyrazolone
- 4-(2-chloro-phenylhydrazono)-1-phenyl-3-methyl-4,5-dihydro-5-pyrazolone
- 4-phenylhydrazono-1-(4-sulfo-phenyl)-3-methyl-4,5-dihydro-5-pyrazolone
- 4-(2-chloro-phenylhydrazono)-1-(2-chloro-phenyl)-3-methyl-4,5-dihydro-5-pyrazolone
- 4-(2-sulfo-phenylhydrazono)-1-(2-chloro-phenyl)-3-methyl-4,5-dihydro-5pyrazolone
- 4-(2-carboxy-phenylhydrazono)-1-phenyl-3-methyl-4,5-dihydro-5-pyrazolone
- 4-(2-hydroxy-4-nitro-5-methylsulfonyl-phenylhydrazono)-3-methyl-4,5-dihydro-1-phenyl-5-pyrazolone
- 4-(2-hydroxy-3-nitro-5-tert-amyl-phenylhydrazono)-3-methyl-1-phenyl-4,5-dihydro-5-pyrazolone
- 4-(2-hydroxy-4-nitro-phenylhydrazono)-3-methyl-1-phenyl-4,5-dihydro-5-pyrazolone.

—10° SYMMETRIC COMPOUNDS KNOWN AS DISAZO COMPOUNDS DEFINED BY THE FOLLOWING FORMULA OR BY THE TAUTOMERIC FORMULA OF THE CORRESPONDING HYDRAZONOQUINONE OR IMINOHYDRAZONE COMPOUNDS WHEN THE DISAZO COMPOUND IS DESCRIBED AS HAVING HYDROXY OR AMINO GROUPS:

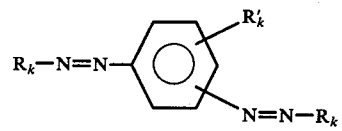

wherein $R_k$ represents a phenyl radical optionally substituted by an amino group or one or two hydroxy and/or methyl radicals; $R'_k$ represents hydrogen or a methyl radical. Examples of such compounds are the following:
- 1,4-bis-(phenylazo)-benzene
- 1,4-bis-(p-tolylazo)-benzene
- 1,3-bis-(4-hydroxy-phenylazo)-benzene
- 1,4-bis-(4-hydroxy-phenylazo)-benzene
- 1,3-bis-(4-amino-phenylazo)-benzene.

—11° SYMMETRIC COMPOUNDS KNOWN AS DISAZO COMPOUNDS DEFINED BY THE FOLLOWING FORMULA OR BY THE TAUTOMERIC FORMULA OF THE CORRESPONDING HYDRAZONOQUINONE OR IMINOHYDRAZONE COMPOUNDS:

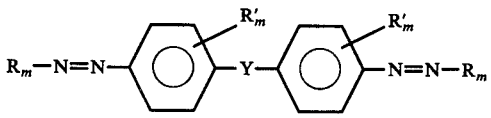

wherein Y represents a direct bond or an oxygen atom or a —CH=CH— or —CH$_2$— group or a —CHR"$_m$— group in which R"$_m$ is a phenyl or chlorophenyl radical; $R_m$ represents a phenyl, naphthyl or 5-pyrazolon-4-yl radical, which radical is optionally substituted by one or two substituents chosen from methyl, phenyl, hydroxy, amino, sulfo and carboxy groups; $R'_m$ represents one or two hydrogen atoms or one or two methyl radicals. Examples of such compounds are the following:
- 4,4'-bis-(4-hydroxy-phenylazo)-2,2'-disulfo-stilbene
- 4,4'-bis-(4-hydroxy-phenylazo)-diphenyloxide
- 4,4'-bis-(2,4-diamino-phenylazo)-diphenyloxide
- 4,4'-bis-(1-amino-4-sulfo-β-napthylazo)-biphenyl
- 4,4'-bis-(3-carboxy-4-hydroxy-phenylazo)-biphenyl
- 4,4'-bis-(4-hydroxy-phenylazo)-diphenylmethane
- 4,4'-bis-(4-hydroxy-3-methyl-3-methyl-phenylazo)-diphenylmethane
- 4,4'-bis-(4-hydroxy-phenylazo)-triphenylmethane
- 4,4'-bis-(4-hydroxy-3-methyl-phenylazo)-triphenylmethane
- α,α-bis-[4-(4-hydroxy-phenylazo)-xylyl]-toluene α, α-bis-[4-(4-hydroxy-3-methyl-phenylazo)-xylyl]-toluene
α, α-bis-[4-(4-hydroxy-phenylazo)-xylyl]-4-chlorotoluene
4,4'-bis-(2-hydroxy-α-naphthylazo)-diphenylmethane
4,4'-bis-(2-hydroxy-α-naphthylazo)-triphenylmethane
α, α-bis-[4-(2-hydroxy-α-naphthylazo)-xylyl]-toluene
α, α-bis[4-(2-hydroxy-α-naphthylazo)-xylyl]-4-chlorotoluene
4,4'-bis-[(5-methyl-2-phenyl-3-pyrazolo/-4-yl)-azo]-3,3'-dimethyl-triphenylmethane.

—12° ASYMMETRIC COMPOUNDS KNOWN AS DISAZO COMPOUNDS DEFINED BY THE FOLLOWING FORMULA OR BY THE TAUTOMERIC FOMULA OF THE CORRESPONDING HYDRAZONOQUINONE OR IMINOHYDRAZONE COMPOUNDS WHEN THE DISAZO COMPOUND IS DESCRIBED AS HAVING AT LEAST ONE HYDROXY OR AMINO GROUP:

$$R_n - N = N - R'_n - N = N - R''_n$$

wherein $R_n$ represents a phenyl, diphenyl or naphthyl radical optionally substituted by one or two substituents chosen from the methyl radical and the hydroxy, carboxy and sulfo groups; $R'_n$ represents a divalent, phenylene or naphthylene radical, optionally substituted by one to three substituents chosen from the methyl radical and the amino, hydroxy, nitro and sulfo groups; $R''_n$ represents a phenyl, naphthyl, tetrahydronaphthyl or dihydro-perimidinyl radical, optionally substituted by one to four substituents chosen from the methyl radical and the hydroxy, sulfo, carboxy and amino groups, the latter may be substituted by a methyl or ethyl radical and/or a sulfamoyl group optionally N-substituted by one or two alkyl radicals having 1 to 4 carbon atoms. Examples of such compounds are the following:

1-(4-phenylazo-phenylazo)-2-naphthol
1-(4-o-tolylazo-2-methyl-phenylazo)-2-naphthol
1-(4-phenylazo-phenylazo)-2-ethylamino-naphthalene
1-(1-phenylazo-4-naphthyl-azo)-2-ethylaminonapthalene
6-(1-phenylazo-4-naphthyl-azo)-2,3-dihydro-2,2-dimethyl-perimidine
2-(4-phenylazo-phenylazo)-4-sulfo-1-naphthol
1-[4-(4-sulfo-phenylazo)-phenylazo]-2-naphthol
2-phenylazo-7-(4-nitro-phenylazo)-8-amino-3,6-disulfo-1-naphthol
1-[4-(4-sulfo-phenylazo)-2-sulfo-phenylazo]-2-naphthol
4-(3-carboxy-4-hydroxy-phenylazo)-4'-(7-amino-1-hydroxy-3-sulfo-β-naphthylazo)-biphenyl
8-(3-carboxy-4-hydroxy-phenylazo)-4'-(7-amino-1-hydroxy-3-sulfo-β-naphthylazo)-biphenyl
1-(4-phenylazo-phenylazo)-4-ethylamino-naphthalene
1-(4-phenylazo-phenylazo)-5,6,7,8-tetrahydro-2-naphthol
1-(2-xylyl-azo-2,4-xylyl-azo)-2-naphthol
1-(4-xylyl-azo-2,4-xylyl-azo)-5,6,7,8-tetrahydro-2-naphthol
1-(4-α-naphthylazo-α-naphthyl-azo)-5,6,7,8-tetrahydro-2-naphthol
1-(4-α-naphthylazo-α-naphthylazo)-2-naphthol
1-(4-phenylazo-phenylazo)-2-hydroxy-6-sulfamoyl-naphthalene
1-(4-phenylazo-phenylazo)-2-hydroxy-6-(N-ethylsulfamoyl)-naphthalene
1-(4-phenylazo-phenylazo)-6-(N-ethylsulfamoyl)-naphthalene
1-(1-phenylazo-4-naphthyl-azo)-b 2-naphthol.

—13° COMPOUNDS KNOWN AS TRIS-AZO OR TETRA-AZO COMPOUNDS DEFINED BY THE FOLLOWING FORMULA OR BY THE TAUTOMERIC FORMULA OF THE CORRESPONDING HYDRAZONOQUINONE OR IMINOHYDRAZONE COMPOUNDS WHEN THE COMPOUND IS DESCRIBED AS HAVING AT LEAST ONE HYDROXY OR AMINO GROUP:

$$R_o - N = N - R'_o - N = N - R''_o - N = N - R'''_o$$

wherein $R_o$ represents a phenyl or naphthyl radical, optionally substituted by one to four substituents chosen from hydroxy carboxy, amino, sulfo and phenylazo or naphthylazo groups, the latter two groups being optionally substituted by one or two substituents chosen from hydroxy, amino, sulfo and nitro groups; $R'_o$ represents a divalent, non-substituted phenylene or diphenylene radical; $R''_o$ represents a divalent phenylene or naphthylene radical, which is non-substituted or substituted by one to four substituents chosen from amino, hydroxy and sulfo groups; $R'''_o$ represents a phenyl or naphthyl radical optionally substituted by one or two substituents by one or two substituents chosen from amino, hydroxy and/or sulfo groups. Examples of such compounds are the following:

1-(4-hydroxy-phenylazo)-4-[7-(phenylazo)-8-amino-3,6-disulfo-1-hydroxy-β-naphthylazo]-benzene
4-(3-carboxy-4-hydroxy-phenylazo)-4'-[3-(4-sulfophenylazo)-2,6-diamino-phenylazo]-biphenyl
4-(4-hydroxy-phenylazo)-4'-[7-(4-nitro-phenylazo)8-amino-3,6-disulfo-1-hydroxy-62 -naphthyalzo]-biphenyl
4-(3,4-diamino-phenylazo)-4'-(2-phenylazo-1-amino-3,6-disulfo-8-hydroxy-β-naphthylazo)-biphenyl
4-[8-(2-hydroxy-α-naphthylazo)-1-hydroxy-3,6--disulfo-β-naphthylazo]-4'-[7-(2-hydroxy-α-naphthylazo)-1-hydroxy-3-sulfo-β-naphthylazo]-biphenyl
4-[8-(2,4-diamino-phenylazo)-1-hydroxy-3,6-disulfo-β-naphthylazo]-4'-[7-(2,4-diamino-phenylazo)-1-hydroxy-3-sulfo-62 -naphthylazo]-biphenyl.

—14° FORMAZYL COMPOUNDS DEFINED BY THE FOLLOWING FORMULA:

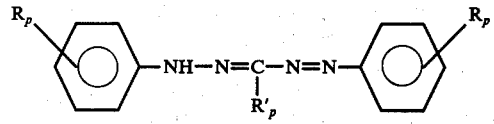

wherein $R_p$ represents hydrogen or a methyl or ethyl radical; $R'_p$ represents a phenyl or benzyl radical or an alkyl radical having 1 to 3 carbon atoms or an alkenyl radical having 2 to 4 carbon atoms. Examples of such compounds are the following:
methylformazyl
ethylformazyl
allylformazyl
4,4'-dimethyl-methylformazyl
4,4'-dimethyl-ethylformazyl
phenylformazyl
benzylformazyl
4,4'-dimethyl-phenylformazyl.

The diazenes employed in the compositions according to the instant invention may also be in the form of their basic and acid salts when such formation is possible.

The diazenes may also be in the form of metal complexes with, for example, chromium, nickel, iron, copper and cobalt; examples of such complexes are the following:

(1:2) chromium complex of 4-(2-hydroxy-4-nitro-5-methyl-sulfonyl-phenylazo)-3-methyl-1-phenyl-5-pyrazolone (1:2) chromium complex of 4-(2-hydroxy-3-nitro-5-tert-amyl-phenylazo)-3-methyl-1-phenyl-5-pyrazolone (1:2) chromium complex of 4-(2-hydroxy-4-nitro-phenylazo)-3-methyl-1-phenyl-5-pyrazolone (1:2) cobalt complex of diazo-(2-amino-4-ethylsulfonyl-phenol)→2-naphthol (1:2) cobalt complex of diazo-(2-amino-4-ethylsulfonylphenol)→2-(N-methoxycarbonyl-N-methylamino)-7-naphthol (1:2) chromium complex of 4-(2-hydroxy-5-nitro-phenylazo)-resorcinol (1:2) cobalt complex of 4-(2-hydroxy-5-nitro-phenylazo)-resorcinol (1:2) chromium complex of 1-(2-hydroxy-5-nitro-phenylazo)-2-naphthol (2:1) chromium complex of 4-(5-chloro-2-hydroxy-phenylazo)-resorcinol (1:2) chromium complex of 1-(2-hydroxy-4-nitro-phenylazo)-2-naphthol (1:2) chromium complex of 4-(2-hydroxy-4-nitro-phenylazo)-resorcinol (1:2) chromium complex of 1-(2-hydroxy-3-nitro-5-tert-amyl-phenylazo)-2-naphthol (1:2) cobalt complex of 4-(5-cloro-2-hydroxy-phenylazo)-resorcinol (1:2) cobalt complex of 4-(2-hydroxy-4-nitro-phenylazo)-resorcinol (1:2) chromium complex of diazo-(2-amino-5-nitro-4-ethylsulfonyl-phenol)→2-(2-carboxy-phenyl)-naphthylamine (1:2) cobalt complex of 1-(2-hydroxy-4-nitro-phenylazo)-2-amino-naphthalene (1:2) chromium complex of diazo-(2-amino-5-nitro-4-ethylsulfonyl-phenol)→8-hydroxy-quinoline (1:2) cobalt complex of diazo-(5-chloro-2-amino-phenol)→3-anilinocarbonyl-2-naphthol (1:2) chromium complex of 1-(2-hydroxy-5-nitro-phenylazo)-2-naphthol (1:2) nickel complex of 1-(2-hydroxy-5-nitro-phenylazo)-2-naphthol (1:2) iron complex of 1-(2-hydroxy-5-nitro-phenylazo)-2-naphthol (1:2) copper complex of 1-(4,6-dichloro-2-hydroxy-phenylazo)-2-naphthol (1:2) chromium complex of 4-(2-hydroxy-5-nitro-phenylazo)-3-methyl-1-phenyl-5-pyrazolone (1:2) cobalt complex of 1-(4,6-dichloro-2-hydroxy-phenylazo)-2-naphthol (1:2) chromium complex of 4-(2-carboxy-phenylazo)-3-methyl-5-pyrazolone (1:2) cobalt complex of 1-(2-hydroxy-5-sulfamoyl-phenylazo)-2-naphthol.

The use of two or several diazenes instead of only one diazene as stabilizing agent C permits to obtain a better stabilization of the phosphoric ester because mixtures of diazenes show synergristic stabilizing properties. The evaporator system according to the present invention can optionally contain a solid or liquid diluent (D) which is a solvent for the insecticidal active substance and/or for the diazene stabilising agent.

The solvents for the phosphoric ester may advantageously be aliphatic alicyclic or aromatic hydrocarbons, which are solid or liquid at ambient temperature with or without pressure. Such solvents may be used separately or in admixture. Their solvent action for the phosphoric ester and/or the stabilising agent can be optionally reinforced by the addition of co-solvents which may be selected from aliphatic ketones, hydroxylated compounds, ethers, esters, amides, nitriles and halogenated hydrocarbons containing at most 12 carbon atoms. Other solvents usable in evaporators according to the present invention are halogenated hydrocarbons containing at most 12 carbon atoms, ethers and esters formed between aliphatic, cycloaliphatic or aralkoylic alcohols or phenols, and aliphatic acids or di-acids such as phthalic acid, sebacic acid or adipic acid, or even non-pesticidal phosphoric esters such as the phosphoric tri-esters of methyl, ethyl, butyl, octyl, decyl, dodecyl, phenyl, cresyl, diphenyl, tert. butylphenyl etc. Solvents used in the evaporators according to the present invention may also be solid compounds, for example synthetic organic resins such as homopolymers and copolymers of vinyl derivatives (acetate, propionates, butyrate, oxides, formal, acetal, butyral, chloride etc.) and/or vinylidene or alkene derivatives (ethylene, propylene, butylene etc.) and/or styrene, and/or vinyl pyrrolidone, and/or cellulose derivatives (metyl oxide, ethyl oxide, benzyl oxide, acetate, propionate, butyrate, phthalates, nitrate, etc.) and/or isoprene and/or butadiene and/or acrylic or methacrylic esters and/or allyl esters (phthalate, isophthalate, maleate, cyanurate, etc) and also synthetic resins of the type arising from the interaction of compounds with reactive groups, as is the case with the so called "epoxy" resins, formed by the condensation of an epoxide with a polyphenol, polyester resins formed by the action of a poly-acid with a polyol, polyurethane resins formed by condensation of a polyisocyanate with a polyol, or coumarone-indene type resins.

Solid compounds serving as solvents may also be natural resins, for example colophony, shellac, tallol or a waxy resin.

Amongst mineral adjuvants which may be introduced into evaporators according to the present invention, the following should be noted: brick, pumice, vermiculite, kaolin, dried clay, calcium carbonate, pyrophllite, dolomite, glass fibre, plaster, talc, natural silica, fossil or otherwise, synthetic silica and metallic oxides. Among inert organic adjuvants which may be introduced into the evaporators according the present invention there should be noted: wood flour, cellulose fibre, starch, maize, faecula, sugars and or diluents with little solvent action should as paraffin, these being optionally modified in their properties by the addition of synthetic organic resins and/or salts formed by alkoylaminoalkoylamines and aliphatic acids, and/or amine derivatives of montmorillonite.

The complementary stabilisers are advantageously selected from sulphur, compounds of divalent sulphur, oxiranes and epoxidized compounds. Evaporators according to the present invention can also contain one or more natural or synthetic aromatic materials, complementary active agents such as an acaricide, an insectifugal agent, a bird-repellent, an antigungal agent or a bactericide.

The evaporator of the invention is constituted by a solid or a liquid disposed on a solid porous of fibrous support. This support may be formed, for example, by a paper, a felt of wool, cotton and/or synthetic fibre, compressed cellulose such as wood fibre, cereals, alfalfa or cotton, a felt card, a card of old papers or a card of glass fibre.

EXPERIMENTS AND EXAMPLES ILLUSTRATING THE INVENTION

The presence of the benzodioxole and of the diazene as stabilizers confers stability to the phosphoric acid ester by water contained in the evaporator used in the ambient humidity, as is shown by the following exemplary experiments:

EXPERIMENT A

Double cards consisting in 5 cm by 10 cm squares cut form a cellulose card made by the French company FIORONI S.A., weighting 905 g/m² at the time of use, and bonded in pairs, back to back, by staples were used.

These doubled cards were divided into six series A - 0 0 to A - 5. Each card A - 0 was impregnated with 12.5g of DDVP. The other double cards were each impregnated with 12.5 g of a solution in DDVP as follows:

A-1 : 1.7% of 1-(4-methyl-2-nitrophenyl azo)-3-4,4-dimethyl-1,2,6-dioxo cyclohexane.
A-2 : 1.7% of 5-allyl benzodioxole.
A-3 : 1% of 5-allyl benzodioxole + 0.7% of 1-(4-methyl-2-nitro phenylazo)-3-ethoxycarbonyl-4,4-dimethyl-2,6-dioxo cyclohexane.
A-4 : 1.7% of 5-(3-oxo-butene-1 yl) benzodioxole.
A-5 : 1% of 5-3-oxo butene-1 yl) benzodioxole + 0.7% of 1-nitro-4 methyl-2 phenylazo-3-ethoxycarbonyl-4, 4-dimethyl-2,6-dioxo-cyclohexane.

The thus impregnated cards were suspended in a room the temperature of which was kept at 22± 2° C, and of which the relative humidity was about 77.

At the end of 21 days, the quantities of DDVP destroyed were measured as given in Experiment A and tabulated as follows:

| A - 0 | A - 1 | A - 2 | A - 3 | A - 4 | A - 5 |
|-------|-------|-------|-------|-------|-------|
| 45.1  | 16.2  | 1.2   | 0.7   | 7.1   | 0.9   |
| ±0.7  | ±1.9  | ±0.3  | ±0.1  | ±1.3  | ±0.1  |

The results of this experiment show the value of mixtures of stabilisers according to the invention. It can in effect be seen from the foregoing results that a synergistic effect is present with these two types of stabilisers.

EXPERIMENT B

Double cards were used as in Experiment A but of size 7 × 10 cm. These cards were divided into two series B-0 and B-1. The doubled cards B-0 were each impregnated with 16.6g of a composition containing 50% by weight DDVP and 50% by weight of a mixture of 3 parts by weight vaseline oil and 1 part by weight stearone.

The double cards B-1 were each impregnated with 16.6g of the same composition but in which 2.1% of the vaseline oil/stearone mixture, based on the weight of the composition, had been replaced by 2% 5-allyl benzodioxole and 0.1% of 1(4-methyl-2-nitro phenylazo)-3-ethoxycarbonyl-4,4-dimethyl-2,6-dioxo cyclohexane.

The so impregnated double cards were each placed in a sachet made from a polyethylene/aluminium complex, the polyethylene face inwards, and the sachets were hermetically sealed by welding. After 8 months storage at 40° C the sachets were opened and their contents submitted to analysis as set out in Experiment A. The percentage quantities of DDVP decomposed were tabulated as follows:

| B - 0 | B - 1 |
|-------|-------|
| 16.7  | 4.9   |

Several formulations will now be described in order to illustrate, though not to limit, the scope of the invention. For simplicity of expression, the benzodioxoles used are denoted as follows:

benzodioxole A : 5-allyl benzodioxole (safrole)
benzodioxole B : 5-(propene-1 yl) benzodioxole
benzodioxole C : 5-hydroxy benzodioxole
benzodioxole D : 5-(3,6,9-trioxa undecyl-2 oxy) benzodioxole
benzodioxole E : 5-(3-oxo butene-1 yl) benzodioxole.

The azoic compounds used as stabilisers are denoted as follows, with the exception of azobenzene which is referred to as such:

diazene A : 1-4(phenylazo phenylazo)2-ethylamino naphthalene
diazene B : 1-(4-methyl-2-nitro phenylazo)-3-ethoxycarbonyl-4,4-dimethyl-2,6-dioxo cyclohexane
diazene C : 1-phenylazo-2-naphthol
diazene D : 1-phenylazo N,N-diethylaniline
diazene E : chromium complex (1 : 2), in admixture of the following azoic compounds:

1-(2-hydroxy-5-nitro phenylazo)-2-naphthol, sodium salt (0.4 mole)
1-(2-hydroxy-4-nitro phenylazo)-2-naphthol, sodium salt (0.3 mole)
1-(2-hydroxy-3-nitro-5-ter, amyl-phenylazo)-2-naphthol sodium salt (0.3 mole).

In the tables in the following examples, values are expressed in weight percent throughout.

EXAMPLE

Insecticidal compositions comprising DDVP as phosphoric ester, and as stabilizer a mixture of a benzodioxole and of an azoic compound, the compositions sometimes also containing a solvent for the ester and/or a complementary stabiliser chosen from sulphur compounds and oxiranes

TABLE I

|                  | 1   | 2   |
|------------------|-----|-----|
| DDVP             | 79  | 78  |
| dioctylphthalate | 20  | —   |
| dibutylsebacate  | —   | 20  |
| octyl epoxystearate | 0.1 | — |
| azobenzene       | 0.1 | —   |
| diazene E        | —   | 0.5 |
| sulphur compound D | — | 0.5 |
| benzodioxole A   | 0.8 | —   |
| benzodioxole E   | —   | 1   |

EXAMPLES 3 to 8

Insecticidal compositions comprising DDVP as phosphoric ester and as stabiliser a mixture of a benzodioxole and of an azoic compound, a vaseline or paraffin oil as solvent, a heavy alkanone as co-solvent, and in some cases a complementary stabiliser chosen from sulpur, sulphur compounds and oxiranes.

TABLE II

| DDVP | 3 | 4 | 5 | 6 | 7 | 8 |
|---|---|---|---|---|---|---|
|  | 50 | 50 | 75 | 75 | 25 | 50 |
| paraffin oil (a') | 35 | 35 | 17 | 17 | 60 | 35 |
| laurone | — | — | 6 | 6 | 12 | — |
| stearone | 11.9 | 11.9 | — | — | — | 12 |
| epoxidised soya oil | — | — | — | — | — | 2 |
| diazene B | 0.1 | 0.1 | — | — | 0.5 | — |
| diazene C | — | — | 0.5 | 0.2 | — | — |
| sulphur | 1 | 1 | — | — | — | 0.1 |
| sulphur compound D | — | — | 0.5 | — | — | — |
| sulphur compound E | — | — | — | 0.8 | — | — |
| benzodioxole A | 2 | — | — | 1 | — | — |
| benzodioxole B | — | 2 | — | — | 1 | 0.9 |
| benzodioxole C | — | — | — | — | 0.5 | — |
| benzodioxole E | — | — | 1 | — | 1 | — |

(a') semi-refined product having a density of 0.870 at 15° C and a viscosity of 1.7° Engler at 50° C.

EXAMPLES 9 to 11

Insecticidal compositions comprising DDVP, a phosphoric ester and as stabilizer a mixture of a benzodioxole and of an azoic compound, a solid or semi-solid adjuvant chosen from paraffin, vaseline and petrolatum, a solvent chosen from heavy alkanones and in some cases a complementary stabiliser chosen grom sulphur compounds and oxiranes.

TABLE III

|  | 9 | 10 | 11 |
|---|---|---|---|
| DDVP | 20 | 28 | 32 |
| ordinary paraffin 60/62° | 53 | — | — |
| vaseline (b) | — | — | 30 |
| petrolatum (b') | — | 35 | — |
| laurone | 24.8 | — | — |
| stearone | — | 36 | 37 |
| epichlorhydrin | — | — | 0.6 |
| diazene D | — | 0.2 | — |
| azobenzene | 2 | — | 0.2 |
| sulphur compound C | — | 0.2 | — |
| benzodioxole A | — | — | 0.2 |
| benzodioxole C | 0.2 | 0.6 | — |

(b) yellow-colored technical product having a dropping point above 47° C.
(b') maroon-colored technical product having a dropping point of about 72° C.

EXAMPLES 12 to 16

Insecticidal compositions usuable in wick evaporators formed by a reservoir and a wick dipping into the composition and having a part open to the atmosphere. These compositions comprise DDVP as phosphoric ester, a solvent for the ester chosen from alkanes, a co-solvent chosen from 1-chlorodecane and 3,6,9-trioxaundecane and as stabiliser a mixture of a benzodioxole and of an azoic compound benzodioxole and in some cases a complementary stabiliser chosen from sulphur compounds and oxiranes.

TABLE IV

| DDVP | 12 | 13 | 14 | 15 | 16 |
|---|---|---|---|---|---|
|  | 9.2 | 10.6 | 7.8 | 7.8 | 10.6 |
| n-dodecane | — | — | 86 | 86 | — |
| "Isopar L" (C') | 85.3 | 84 | — | — | 84 |
| 1-chloro decane | — | — | 6 | 6 | — |
| 3,6,9-trioxa undecane (c) | 5 | 5 | — | — | 5 |
| epoxidised soya oil | — | — | — | — | 0.25 |
| diazene A | 0.04 | 0.05 | — | 0.04 | — |
| azobenzene | — | 0.1 | 0.1 | — | 0.05 |
| sulphur compound A | — | — | — | 0.06 | — |

TABLE IV-continued

| DDVP | 12 | 13 | 14 | 15 | 16 |
|---|---|---|---|---|---|
|  | 9.2 | 10.6 | 7.8 | 7.8 | 10.6 |
| benzodioxole B | 0.46 | — | 0.1 | — | 0.1 |
| benzodioxole C | — | 0.25 | — | 0.1 | — |

(c) reinforcing solvent known as diglycoldiethyl ether, and sold under the Trake Mark "Diethylcarbitol" by the U.S. Company Union Carbide Chemicals Co. of New York.
(c') distillation cut between 189° and 205° C of branched aliphatic hydrocarbons obtained by synthesis, containing a mixture of decane, undecane and dodecane, sold by the company Esso Standard.

EXAMPLES 17 and 18

Insecticidal compositions comprising DDVP as phosphoric ester, as stabiliser a mixture of a benzodioxole and of an azoic compound, an odorant material chosen from ionone and orange terpenes and in some cases an oxirane as complementary stabiliser.

TABLE V

|  | 17 | 18 |
|---|---|---|
| DDVP | 77 | 72 |
| α-ionone | 20 | 5 |
| orange terpenes | — | 20 |
| epoxidised soya oil | — | 2 |
| diazene A | 0.5 | — |
| diazene B | — | 0.5 |
| benzodioxole B | — | 0.5 |
| benzodioxole E | 2.5 | — |

EXAMPLES 19 and 20

Insecticidal compositions comprising DDVP as phosphoric ester, at least one benzodioxole and a diazene as stabiliser, a synthetic thermoplastic resin as solid solvent, a heavy ester used as complementary solvent, in some cases as a plasticiser for the resin, and in several cases as complementary stabiliser from sulphur compounds.

TABLE VI

|  | 19 | 20 |
|---|---|---|
| DDVP | 25 | 30 |
| polyvinyl chloride | 62 | — |
| vinyl acetate/vinyl chloride copolymer (10:90) | — | 50 |
| tricresyl phosphate | 10 | 19 |
| diazene C | 0.2 | 0.1 |
| sulphur compound B | 0.3 | — |
| benzodioxole B | — | 0.9 |
| benzodioxole E | 2.5 | — |

EXAMPLES 21 to 23

Insecticidal compositions comprising DDVP as phosphoric ester, as stabiliser a mixture of a benzodioxole and of an azoic compound, a paraffin as solid adjuvant, a fossil silica as mineral adjuvant, and, in some cases, a complementary stabiliser consisting in a sulphur compound, an ethylene/vinyl acetate copolymer as an agent improving the mechanical properties of the paraffin, a pigment and/or the modified montmorillonite as dispersant allowing the composition to remain homogeneous before cooling.

TABLE VII

|  | 21 | 22 | 23 |
|---|---|---|---|
| DDVP | 24 | 24 | 25 |
| paraffin 60/62° | 65 | 57 | 52 |

TABLE VII-continued

|  | 21 | 22 | 23 |
|---|---|---|---|
| DDVP | 24 | 24 | 25 |
| ethylene/vinyl acetate copolymer (71:29) | — | — | 12 |
| diatomaceous earth | — | 12 | 10 |
| amine oleate (e') | — | 5 | — |
| modified montmorillonite (e") | 9 | — | — |
| pigment (e) | 0.5 | — | — |
| azobenzene | — | 1 | — |
| diazene B | 0.4 | — | 0.5 |
| sulphur compound F | 0.3 | — | — |
| benzodioxole A | — | — | 0.5 |
| benzodioxole B | — | 1 | — |
| benzodioxole E | 0.8 | — | — | e) yellow Irgalith BAW
e') product formed by reaction, in a molecular ratio of 2:1 between oleic acid and a mixture of the following diamines: hexadecylaminopropylene amine (10%) octadecylamino propylene amine (50%) octadecylamino propylene amine (85%)
e") mixture of dimethyl dihexadecylammonium montmorillonite (70%) and dimethyl dioctadecylammonium montmorillonite.

It is clear that the invention is not limited to the formulations just set forth, which are merely given as examples of the manifold possibilities of use of the invention. In particular, the DDVP of these formulations can be replaced by a phosphoric ester chosen from:
1. 2,2-dichloro vinyl dimethyl phosphate
2. 2,2-dichloro vinyl diethyl phosphate
3. 2,2-dichloro vinyl dipropyl phosphate
4. 2,2-dibromo vinyl dimethyl phosphate
5. 2,2-dibromo vinyl diethyl phosphate
6. 2,2-dibromo vinyl dipropyl phosphate
7. 2-bromo-2-chloro vinyl dimethyl phosphate
8. 2-bromo-2-chloro vinyl diethyl phosphate
9. 2,2-dichloro vinyl, ethyl methyl phosphate
10. 1,2-dibromo-2,2-dichloro ethyl dimethyl phosphate
11. 1,2-dibromo-2,2-dichloro ethyl diethyl phosphate
12. 1-bromo-2,2,2-trichloro ethyl dimethyl phosphate
13. 1-bromo-2,2,2-trichloro ethyl diethyl phosphate
14. 1,2,2,2-tetrabromo ethyl dimethyl phosphate
15. 1,2,2,2-tetrabromo ethyl diethyl phosphate
16. 1,2-dibromo-2,2-dichloro propyl dimethyl phosphate
17. 1,2-dibromo-2,2-dichloro propyl diethyl phosphate
18. 2,2-dichloro 1-methyl vinyl dimethyl phosphate
19. 2,2-dichloro 1-methyl vinyl diethyl phosphate and the corresponding thiophosphates, for example
20. 2,2-dichloro vinyl dimethyl thiophosphate.

We claim:
1. An insecticide evaporator comprising:
   I. a solid or liquid insecticidal composition containing
      A. an insecticidally effective amount of insecticidal phosphate selected from the group consisting of
         2,2-dichlorovinyl dimethyl phosphate
         2,2-dichlorovinyl diethyl phosphate
         2,2-dichlorovinyl dipropyl phosphate
         2,2-dibromovinyl dimethyl phosphate
         2,2-dibromovinyl diethyl phosphate
         2,2-dibromovinyl dipropyl phosphate
         2-bromo-2-chlorovinyl dimethyl phosphate
         2-bromo-2-chlorovinyl diethyl phosphate
         2,2-dichlorovinyl ethyl methyl phosphate
         2,2-dichloro-1-methyl-vinyl dimethyl phosphate and
         2,2-dichloro-1-methyl-vinyl diethyl phosphate,
      wherein on contact with molecules of water at least partial decomposition of the ester takes place by protonization, said vinyl phosphate being or not being admixed with a solid or liquid solvent,
      B. about 0.1 to 10%, based on the weight of said volatile phosphate, of a 1,3-benzodioxole capable of stabilizing said phosphate against decomposition by protonization, said benzodioxole having no action as a toxicity synergist for the insecticidal phosphate in said proportions, and selected from the group consisting of at least one compound of the formula

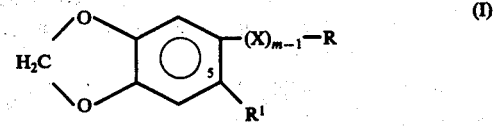

(I)

wherein $m$ is 1 or 2, and X is an alkylene bridge of 1 to 2 or an alkylene bridge of 2 carbon atoms, and R' is
   a. hydrogen or
   b. lower alkyl and
A. when $m$ represents 1 in formula (I) R represents
   a. hydrogen
   b. lower alkyl
   c. lower alkenyl
   d. halogen of atomic number not exceeding 17
   e. nitro
   f. the group

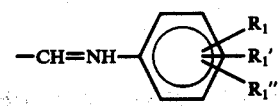

in which each of $R_1$, $R_1'$ and $R_1''$, independently of the others, is the same or a different group selected from the group consisting of hydrogen, lower alkyl, lower alkoxy, chloro and bromo;
   g. the group

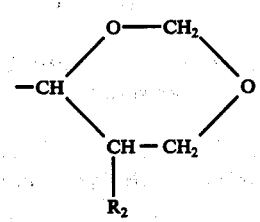

in which $R_2$ is hydrogen or lower alkyl, or
   h. the group

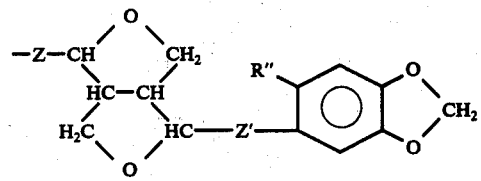

in which Z and Z' are each independently a C—C bond or an oxygen atom (—O—) and R" is hydrogen, lower alkyl or lower alkoxy, and
B. when m represents 1 or 2 in formula (I)
R represents
   i. cyano ii. the group

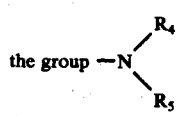 (ii)

wherein R₄ is hydrogen or lower alkyl and R₅ is hydrogen or lower alkyl, iii. the group —CO-R₆ in which R₆ is
a. hydrogen
b. —OM in which M is hydrogen or an equivalent metal cation or cation or a guaternary ammonium
c. lower alkyl or
d. lower alkoxy
e. phenyl, unsubstituted or substituted by one or more of the following substituents: lower alkyl, lower alkoxy, chloro, bromo;

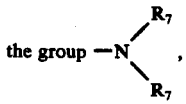 f)

wherein each of R₇ and R₇' is independently selected from hydrogen or lower alkoxy

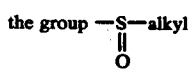 (iv)

in which the alkyl group has 1 to 8 carbon atoms v. the group —O—R₈ in which R₈ is lower alkyl or oxa alkyl of at most 15 carbon atoms and 3 oxygen atoms in the chain,

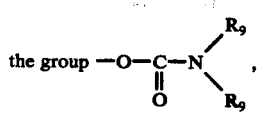 (vi)

in which each of R₉ and R₉'' independently is hydgrogen, lower alkyl or phenyl or vii. nitro C. when m represents 1 in formula (I):
R and R' taken together represent one of the following divalent groups:
a. the group

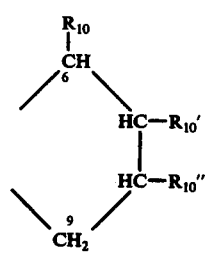

in which each of R₁₀, R₁₀, and R₁₀'' independently is hydrogen, lower alkyl, alkoxycarbonyl of 2 to 5 carbon atoms, or the group -COOM, M having the meaning given above, or b. the group

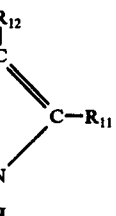

in which R₁₁ is
hydrogen, lower alkyl, lower alkoxy or pyrrolidino, and R₁₂ represents
hydrogen or lower alkyl, C. about 0.1 to 10% by weight based on the weight of said vinyl phosphate of at least one secondary agent for stabilizing said phosphate against decomposition by protonization selected from the group consisting of at least one diazene compound of the formula 1. monoazo compounds defined by the following formula:

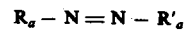

$$R_a - N = N - R'_a$$

wherein $R_a$ and $R'_a$ are the same or different and each represents phenyl, naphthyl, pyridyl, quinolyl or diphenyl;

2. mono-azo compound defined by the following formula:

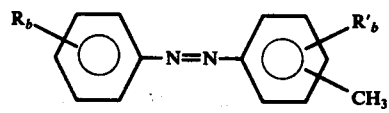

wherein $R_b$ represents hydrogen or one or two methyl radicals, $R'_b$ represents hydrogen or methyl, 3. mono-azo compound defined by the following formula:

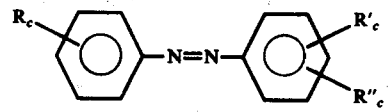

wherein $R_c$ represents hydrogen or one or two halogens, $R'_c$ represents halogen, and $R''_c$ represents hydrogen or halogen, halogen being chlorine, bromine, fluorine or iodine, 4. mono-azo compound defined by the following formula:

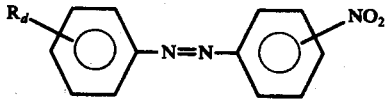

wherein $R_d$ represents hydrogen or nitro, 5. mono-azo amino compound defined by the following formula or by the tautomeric formula of the corresponding imino-hydrazone compounds:

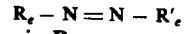

$$R_e - N = N - R'_e$$

wherein $R_e$ represents a phenyl or naphthyl substituted by one or two amino groups which are unsubstituted or substituted by acetyl or benzoyl, by one or two phenyl or benzyl or by alkyl having 1 to 4 carbon atoms, the radical $R_e$ being unsubstituted or further substituted by one to three substituents selected from the group consisting of alkyl having 1 to 5 carbon atoms, chlorine, nitro, alkoxy having 1 to 3 carbon atoms, alkylsulfonyl having 1 to 4 carbon atoms and sulfamoyl, the latter being unsubstituted or N-substituted by one or two alkyl having 1 to 4 carbon atoms; $R'_e$ represents phenyl, naphthyl or pyrazolyl, unsubstituted or substituted by one to three substituents selected from the group consisting of methoxy, ethoxy, propoxy, methyl, ethyl, phenyl, cyclohexyl, chlorine, nitro and amino, the latter being unsubstituted or substituted by one or two phenyl, benzyl or alkyl having 1 to 4 carbon atoms, 6. mono-azo compounds defined by the following formula or by the tautomeric formula of the corresponding hydrazonoquinone compounds:

wherein $R_f$ represents phenyl, naphthyl or quinolyl having one or two hydroxy groups and being unsubstituted or substituted by one to three further substituents selected from the group consisting of chlorine, alkyl having 1 to 5 carbon atoms, cyclohexyl, carbamoyl, carboxy and nitro; $R'_f$ represents a phenyl, naphthyl or pyridyl, unsubstituted or substituted by one to four substituents selected from the group consisting of chlorine, cyclohexyl, methyl, hydroxy, nitro, methoxy, benzyloxy, dimethylamino and dimethylaminomethyl, 7. mono-azo compounds defined by the following formula:

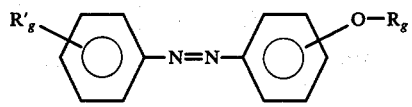

wherein $R_g$ represents alkyl of 1 to 4 carbon atoms or alkanoyl of 2 to 18 carbon atoms, $R'_g$ represents hydrogen or alkoxy of 1 to 4 carbon atoms, 8. phenylhydrazone compound defined by the following formula:

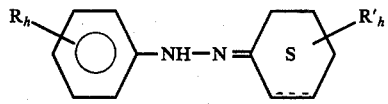

wherein $R_h$ represents hydrogen or one or two substituents selected from the group consisting of chlorine and nitro; $R'_h$ represents hydrogen or one to three alkyl each of 1 to 4 carbon atoms; the dotted line represents an optional second bond, 9. phenylhydrazone compounds defined by the following formula or by the tautomeric formula of the corresponding hydroxyazo compounds:

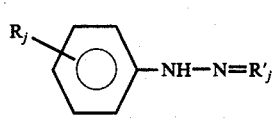

wherein $R_j$ represents one to three substituents selected from the group consisting of alkyl having 1 to 5 carbon atoms, chlorine, nitro, hydroxy, carboxy, sulfo and methylsulfonyl; $R'_j$ represents a 2-indolinon-3-ylidene or a 3,4-dihydro-3-pyrazolon-4-ylidene radical, unsubstituted or substituted by methyl, phenyl, chlorophenyl or sulfophenyl, 10. symmetric compounds defined by the following formula or by the tautomeric formula of the corresponding hydrazonoquinone or iminohydrazone compounds when the disazo compound is described as having hydroxy or amino groups;

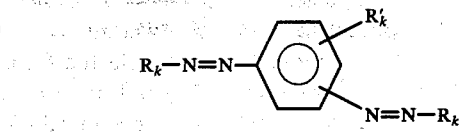

wherein $R_k$ represents phenyl unsubstituted or substituted by amino or one or two substituents which are hydroxy or methyl; $R'_k$ represents hydrogen or methyl, 11. symmetric compounds defined by the following formula or by the tautomeric formula of the corresponding hydrazonoquinone or imminohydrazone compounds:

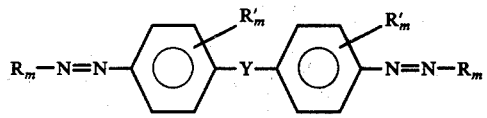

wherein Y represents a direct bond or an oxygen atom or a —CH=CH— group or —CH$_2$— group or a —CHR''$_m$— group in which R''$_m$ is phenyl or chlorophenyl; $R_m$ represents a phenyl, naphthyl or 5-pyrazolon-4-yl, which is unsubstituted or substituted by one or two substituents selected from the group consisting of methyl, phenyl, hydroxy, amino, sulfo and carboxy; $R'_m$ represents one or two hydrogen or one or two methyl, 12. polyazo compounds defined by the following formula or by the tautomeric formula of the corresponding hydrazonoquinone or iminohydrazone compounds when the disazo compound is defined as having at least one hydroxy or amino group:

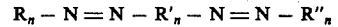

wherein $R_n$ represents phenyl, diphenyl or naphthyl unsubstituted or substituted by one or two substituents selected from the group consisting of methyl, hydroxy, carboxy and sulfo; $R'_n$ represents divalent phenylene or naphthylene, unsubstituted or substituted by one to three substituents selected from the group consisting of methyl, amino, hydroxy, nitro and sulfo; $R''_n$ represents a phenyl, naphthyl, tetrahydronaphthyl or dihydropyrimidinyl, unsubstituted or substituted by one to four substituents selected from the group consisting of methyl, hydroxy, sulfo, carboxy and amino, the latter being unsubstituted or substituted by methyl or ethyl, and sulfamoyl unsubstituted or N-substituted by one or two alkyl having 1 to 4 carbon atoms, 13. tris-azo or tetra-azo compounds defined by the following formula or by the tautomeric formula of the corresponding hydrazonoquinone or iminohydrazone compounds when the compound is defined as having at least one hydroxy or amino:

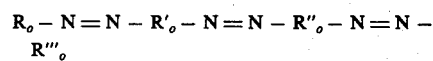

wherein $R_o$ represents phenyl or naphthyl, unsubstituted or substituted by one to four substituents selected from the group consisting of hydroxy, carboxy, amino, sulfo, phenylazo and naphthylazo, the latter two being unsubstituted or substituted by one or two substitutents selected from the group consisting of hydroxy, amino, sulfo and nitro; $R'_o$ represents a divalent, unsubstituted phenylene or diphenylene; $R''_o$ represents a divalent phenylene or naphthylene which is unsubstituted or substituted by one to four substitutents selected from the group consisting of amino, hydroxy and sulfo; $R'''_o$ represents a phenyl or naphthyl unsubstituted or substituted by one or two substitutents selected from the group consisting of amino, hydroxy, and sulfo, 14. formazyl compounds defined by the following formula:

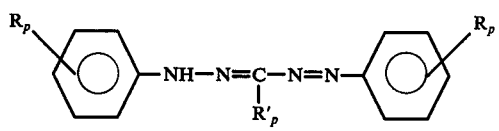

wherein $R_p$ represents hydrogen, methyl or ethyl; $R'_p$ represents phenyl, benzyl, alkyl having 1 to 3 carbon atoms or alkenyl having 2 to 4 carbon atoms, D. a salt of a compound as defined under (C) above having at least one group capable of salt formation or, E. a metal complex of a compound or salt as defined under (C) or (D) bearing one or two groups capable of metal complex formation selected from the group consisting of hydroxy, carboxy, amino, mono ($C_1$–$C_4$ alkyl) amino, phenylamino, phenylsulphonamino and ($C_1$–$C_4$ alkyl) sulfonamido, said diazene being soluble in said composition, II. a solid fibrous support absorbent for the composition (I) formed by a felt of wool, a cellulosic fiber material or a cardboard of glass fibers.

2. An insecticide evaporator as in claim 1, wherein the proportion of the stabilizing agents (B) and (C) is 0.5 to 6% of the weight of the phosphoric ester.

3. An insecticide evaporator as in claim 1, further comprising (III) a solid or liquid solvent for the phosphoric ester (I) which solvent is selected from the group consisting of vaseline oil, paraffin oil, petrolatum, n-dodecane, branched aliphatic $C_{10}$–$C_{12}$ hydrocarbons having a distillation cut between 189° and 205° C, 1-chloro-decane, 3,6,9-trioxaundecane, dioctylphthalate, dibutylsebacate, tricresylphosphate, laurone, stearone, α-ionone, orange terpenes, a polyvinyl chloride polymer, a vinyl acetate/vinyl chloride and an ethylene/vinyl acetate copolymer.

4. An insecticide evaporator as in claim 1, further comprising as an inert mineral adjuvant diatomaceous earth.

5. An insecticide evaporator as in claim 1, further comprising an epoxidized compound selected from the group consisting of octylepoxystearate, epoxidized soya oil and epichlorhydrin in a proportion of 0.1 to 20% based on the weight of said volatile phosphoric ester.

6. An insecticide evaporator as in claim 1, further comprising a permeable membrane as a lining for said support.

7. An insecticide evaporator as in claim 1, wherein said permeable membrane is constituted by a layer of polyethylene or polypropylene or a mixture thereof or a copolymer comprising vinylidene chloride.

8. An insecticide evaporator as in claim 1, wherein said permeable membrane is constituted by a layer of polyethylene of a thickness of from 10 to 80 microns.

9. An insecticide evaporator as in claim 1, wherein said stabilising agent consists essentially of
  i. a benzodioxole (B) substituted by an unsaturated aliphatic group and
  ii. said diazene.

* * * * *